United States Patent
Tandikul et al.

(10) Patent No.: US 12,359,154 B2
(45) Date of Patent: Jul. 15, 2025

(54) METHODS FOR CULTIVATING TISSUE ON POROUS SUBSTRATES

(71) Applicant: Upside Foods, Inc., Berkeley,, CA (US)

(72) Inventors: Napat Tandikul, Berkeley, CA (US); Nicholas J. Genovese, Berkeley, CA (US)

(73) Assignee: Upside Foods, Inc., Berkeley, CA (US)

( * ) Notice: Subject to any disclaimer, the term of this patent is extended or adjusted under 35 U.S.C. 154(b) by 50 days.

(21) Appl. No.: 18/409,567

(22) Filed: Jan. 10, 2024

(65) Prior Publication Data
US 2024/0141268 A1  May 2, 2024

Related U.S. Application Data

(63) Continuation of application No. 17/131,483, filed on Dec. 22, 2020, now Pat. No. 11,912,967.

(51) Int. Cl.
| | |
|---|---|
| C12M 3/00 | (2006.01) |
| C12M 1/00 | (2006.01) |
| C12M 1/12 | (2006.01) |
| C12M 1/42 | (2006.01) |

(52) U.S. Cl.
CPC ............ *C12M 21/08* (2013.01); *C12M 25/14* (2013.01); *C12M 29/10* (2013.01); *C12M 35/02* (2013.01); *C12M 35/04* (2013.01)

(58) Field of Classification Search
CPC ...... C12M 21/08; C12M 25/14; C12M 25/02; C12M 29/10; C12M 35/02; C12M 35/04; C12M 41/00; C12M 41/40
See application file for complete search history.

(56) References Cited

U.S. PATENT DOCUMENTS

| | | |
|---|---|---|
| 6,197,575 B1 | 3/2001 | Griffith et al. |
| 2011/0250585 A1 | 10/2011 | Ingber et al. |
| 2012/0030548 A1 | 2/2012 | Zhang |
| 2013/0030548 A1* | 1/2013 | Ling ............... A61L 27/3808 435/395 |
| 2014/0199679 A1 | 7/2014 | Panoskaltsis et al. |
| 2020/0056144 A1* | 2/2020 | Castillo ............... C12M 25/02 |
| 2022/0195359 A1* | 6/2022 | Lavon ............... C12M 41/26 |
| 2022/0195368 A1 | 6/2022 | Genovese |

FOREIGN PATENT DOCUMENTS

| | | |
|---|---|---|
| JP | 2011172533 A | 9/2011 |
| KR | 1020200141869 A | 12/2020 |
| WO | 2012/140519 A2 | 10/2012 |
| WO | 2015/066377 A1 | 5/2015 |
| WO | 2020/163329 | 8/2020 |

OTHER PUBLICATIONS

International Search Report & Written Opinion as received in PCT/US2021/064080 dated Apr. 12, 2022.
U.S. Appl. No. 17/131,483, filed Mar. 22, 2023.
U.S. Appl. No. 17/131,483, filed Jul. 5, 2023.
U.S. Appl. No. 17/131,483, filed Oct. 16, 2023.

* cited by examiner

*Primary Examiner* — Michael L Hobbs
(74) *Attorney, Agent, or Firm* — Keller Preece PLLC

(57) ABSTRACT

Described herein are novel systems and methods for biomanufacturing, such as tissue cultivation. In some variations the systems and methods may comprise at least one porous substrate.

20 Claims, 10 Drawing Sheets

METHODS FOR CULTIVATING TISSUE ON POROUS SUBSTRATES

CROSS-REFERENCE TO RELATED APPLICATIONS

The present application is a continuation of U.S. application Ser. No. 17/131,483, filed on Dec. 22, 2020, entitled "SYSTEMS AND METHODS FOR CULTIVATING TISSUE ON POROUS SUBSTRATES." The aforementioned application is hereby incorporated by reference in its entirety.

TECHNICAL FIELD

This invention relates generally to the field of biomanufacturing, such as for cultivating tissue.

BACKGROUND

Meat produced by culturing metazoan cells (e.g., cell-based meat, in vitro produced cell-based meat, cell culture-based meat, in vitro meat, cultured meat, lab-grown meat, or clean meat) is moving closer to the marketplace. Compared to traditional slaughter-based animal meat, cell-based meat has several nutritional, environmental and safety-related advantages. However, challenges in biomanufacturing processes at industrial scale currently impede the broad application of cell-based meat, such as the unscheduled detachment of tissue biomass during cultivation due to insufficient anchorage to the cultivation substrate, contact inhibition of cell growth, limited supply of nutrients, and poor elimination of metabolic waste. As a result, overall harvestable yield is reduced, batch-to-batch product variability arises, and cost efficiency declines.

Accordingly, there is a need for new and improved systems for the biomanufacturing of meat. Provided herein are novel systems and methods for the optimal cultivation of meat that overcome these and related challenges.

SUMMARY

Generally, a system for cultivating tissue may comprise a bioreactor, a porous substrate arranged in the bioreactor and comprising at least one conduit extending between a first surface of the substrate and a second surface of the substrate opposite the first surface.

In some variations of the system the substrate may comprise at least one material selected from the group consisting of: silicate, ceramic, carbon allotrope, metal, metallic alloy, synthetic polymer, biological polymer, synthetically-modified biological polymer, composite, and resin. In some variations of the system the substrate may comprise at least one porous architecture selected from the group consisting of: continuous, gradient, granular, fibrous, spun, woven, stratified, fritted, sintered, bored, channeled, polygonal, spheroid, inverse spheroid, bifurcated between primary and secondary structures, linear, tortuous, periodic, patterned and stochastic.

In some variations of the system the substrate may have a tortuosity with an average arc-to-chord length ratio of about 1.0-1.2, 1.2-1.4, 1.4-1.6, 1.6-1.8, 1.8-2.0, 2-3, 3-4, 4-5, 5-6, 6-7, 7-8, 8-9 or 9-10.

In some variations of the system the at least one conduit may have a pore size of between about 0.01 nm-1 nm, 0.1 nm-0.5 nm, 0.5 nm-1 nm, 1 nm-5 nm, 5 nm-10 nm, 10 nm-20 nm, 20 nm-40 nm, 40 nm-80 nm, 80 nm-160 nm, 160 nm-320 nm, 320 nm-640 nm, 0.64 µm-1.2 µm, 1.2 µm-2.4 µm, 2.4 µm-4.8 µm, 4.8 µm-9.6 µm, 9.6 µm-19.2 µm, 19.2 µm-38.4 µm, 38.4 µm-76.8 µm, 76.8 µm-153.6 µm, 153.6 µm-307.2 µm, 307.2 µm-614.4 µm, or 0.6144 mm-1.2 mm.

In some variations of the system the porosity of the substrate may be between about 0.1%-0.25%, 0.25%-0.50%, 0.50%-1.0%, 1.0%-2.5%, 2.5%-5.0%, 5.0%-10%, 10%-20%, 20%-30%, 30%-40%, 40%-50%, 50%-60%, 60%-70%, 70%-80%, 80%-90%, 90%-95% or 95%-99% of the substrate volume.

In some variations of the system the substrate may comprise a mean axial thickness of between about 25 µm-50 µm, 50 µm-100 µm, 100 µm-200 µm, 200 µm-400 µm, 400 µm-800 µm, 800 µm-1600 µm, 1.6 mm-3.2 mm, 3.2 mm-6.4 mm, 6.4 mm-12.8 mm, 1.28 cm-2.56 cm or 2.56 cm-5.12 cm.

In some variations of the system the substrate may have a width of between about 0.5 mm-1.0 mm, 1.0 mm-2.0 mm, 2.0 mm-4.0 mm, 4.0 mm-8.0 mm, 0.8 cm-1.6 cm, 1.6 cm-3.2 cm, 3.2 cm-6.4 cm, 6.4 cm-12.8 cm, 12.8 cm-25.6 cm, 25.6 cm-51.2 cm, 0.5 m-1.0 m, 1 m-2 m, 2 m-4 m, 4 m-8 m, 8 m-16 m, 16 m-32 m, or 32 m-64 m.

In some variations the system may comprise a plurality of porous substrates arranged in the bioreactor. In some variations of the system the first surface of the substrate may be parallel to a flow direction associated with an inlet of the bioreactor. In some variations of the system the first surface of the substrate may be non-parallel to a flow direction associated with an inlet of the bioreactor. In some non-parallel variations of the system, the first surface of the substrate may be oriented at an angle of between about 60 degrees and 120 degrees relative to the flow direction associated with the inlet. In some non-parallel variations of the system, the first surface of the substrate may be oriented at about 90 degrees relative to the flow direction associated with the inlet.

In some variations the system may further comprise a vessel in fluidic communication with the bioreactor. In some variations the system may further comprise a fluidic control system for controlling fluid flow between the vessel and the bioreactor. In some variations the vessel may be configured to hold a cell culture medium.

Further, a method for cultivating tissue may comprise seeding metazoan cells onto a porous substrate, wherein the porous substrate comprises at least one conduit extending between a first surface of the substrate and a second surface of the substrate opposite the first surface; and culturing the metazoan cells on the porous substrate.

In some variations the method comprises seeding metazoan cells onto a porous substrate disclosed herein and culturing the metazoan cells on the porous substrate.

In some variations of the method the substrate may comprise at least one material selected from the group consisting of: silicate, ceramic, carbon allotrope, metal, metallic alloy, synthetic polymer, biological polymer, synthetically-modified biological polymer, composite, and resin.

In some variations of the method the substrate may comprise at least one porous architecture selected from the group consisting of: continuous, gradient, granular, fibrous, spun, woven, stratified, fritted, sintered, bored, channeled, polygonal, spheroid, inverse spheroid, bifurcated between primary and secondary structures, linear, tortuous, periodic, patterned and stochastic.

In some variations of the method the substrate may have a tortuosity with an average arc-to-chord length ratio of about 1.0-1.2, 1.2-1.4, 1.4-1.6, 1.6-1.8, 1.8-2.0, 2-3, 3-4, 4-5, 5-6, 6-7, 7-8, 8-9 or 9-10.

In some variations of the method porosity of the substrate may be between about 0.1%-0.25%, 0.25%-0.50%, 0.50%-1.0%, 1.0%-2.5%, 2.5%-5.0%, 5.0%-10%, 10%-20%, 20%-30%, 30%-40%, 40%-50%, 50%-60%, 60%-70%, 70%-80%, 80%-90%, 90%-95% or 95% to 99% of the substrate volume.

In some variations of the method the substrate may comprise a mean axial thickness of between about 25 µm-50 µm, 50 µm-100 µm, 100 µm-200 µm, 200 µm-400 µm, 400 µm-800 µm, 800 µm-1600 µm, 1.6 mm-3.2 mm, 3.2 mm-6.4 mm, 6.4 mm-12.8 mm, 1.28 cm-2.56 cm or 2.56 cm to 5.12 cm.

In some variations of the method the substrate may have a width of between about 0.5 mm-1.0 mm, 1.0 mm-2.0 mm, 2.0 mm-4.0 mm, 4.0 mm-8.0 mm, 0.8 cm-1.6 cm, 1.6 cm-3.2 cm, 3.2 cm-6.4 cm, 6.4 cm-12.8 cm, 12.8 cm-25.6 cm, 25.6 cm-512 cm, 0.5 m-1.0 m, 1 m-2 m, 2 m-4 m, 4 m-8 m, 8 m-16 m, 16 m-32 m, or 32 m-64 m.

In some variations of the method a plurality of porous substrates may be arranged in the bioreactor.

In some variations of the method the first surface of the substrate may be parallel to a flow direction associated with an inlet of the bioreactor. In some variations of the method the first surface of the substrate may be non-parallel to a flow direction associated with an inlet of the bioreactor. In some non-parallel variations of the method the first surface of the substrate may be oriented at an angle of between about 60 degrees and 120 degrees relative to the flow direction associated with the inlet. In some non-parallel variations of the method the first surface of the substrate may be oriented at about 90 degrees relative to the flow direction associated with the inlet.

In some variations of the method the porous substrate may be arranged in a bioreactor. In some variations of the method seeding metazoan cells may comprise directing at least a portion of the metazoan cells toward the substrate in a first direction extending from the first surface to the second surface, and directing at least a portion of the metazoan cells toward the substrate in a second direction extending from the second surface to the first surface. In some variations of the method seeding metazoan cells may comprise alternately directing metazoan cells in the first direction and the second direction.

In some variations seeding metazoan cells comprises seeding an initial cell density on the porous substrate. In some variations the substrate is treated with one or more focal adhesion motifs prior to seeding.

In some variations seeding metazoan cells comprises alternately directing metazoan cells in the first direction and/or the second direction.

In some variations of the method seeding metazoan cells may comprise seeding metazoan cells of a first cell type on the first surface, and seeding metazoan cells of a second cell type on the second surface, wherein the second cell type is different from the first cell type.

In some variations of the method culturing metazoan cells may comprise facilitating transfer, through the substrate, of at least one secreted product of the metazoan cells on the first surface to the metazoan cells on the second surface. In some variations of the method culturing the metazoan cells comprises directing motility, through the substrate, of at least one seeded cell population from the first surface to the second surface. In some variations of the method cells seeded onto the first surface and directed to the second surface are cultivated into tissues on the second surface.

In some variations of the method culturing metazoan cells may comprise perfusing a liquid cell culture medium through the substrate.

In some variations, perfusing the liquid cell culture medium may comprise applying the liquid cell culture medium in a flow direction that is parallel to the first surface of the substrate.

In some variations, perfusing the liquid cell culture medium may comprise applying the liquid cell culture medium in a flow direction that is non-parallel to the first surface of the substrate. In some non-parallel variations, the flow direction may be angled between about 60 degrees and 120 degrees relative to the first surface of the substrate. In some non-parallel variations, the flow direction may be angled about 90 degrees relative to the first surface of the substrate.

In some variations culturing the metazoan cells may comprise perfusing the liquid cell culture medium across a pressure differential between the first surface and the second surface. In some variations perfusing the liquid cell culture medium through the substrate may comprise applying the liquid cell culture medium in a first direction extending from the first surface of the substrate to the second surface, and applying the liquid cell culture medium in a second direction extending from the second surface to the first surface.

In some variations culturing the metazoan cells may comprise perfusing the liquid cell culture medium in a flow direction that is tangential to at least one of the first surface and the second surface of the substrate.

In some variations culturing metazoan cells may comprise cultivating the metazoan cells into a comestible meat product. In some variations the metazoan cell species may comprise vertebrate, invertebrate, crustacean, livestock, poultry, game, aquatic species, terrestrial species, or amphibious species.

DETAILED DESCRIPTION

Figure 1A:
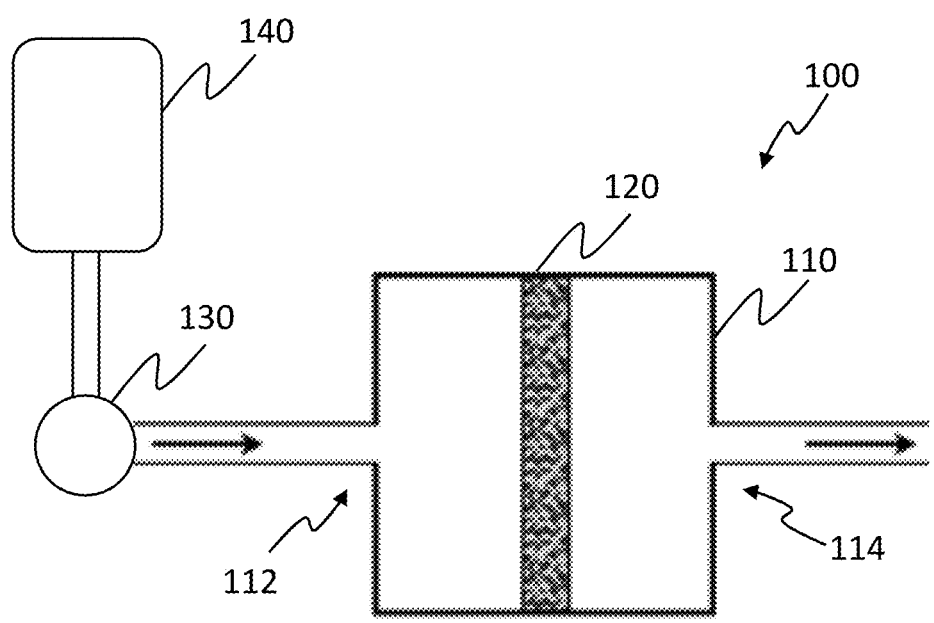
FIG. 1A depicts an illustrative schematic of an exemplary system for cultivating tissue comprising a bioreactor and a porous substrate.

Non-limiting examples of various aspects and variations of the invention are described herein and illustrated in the accompanying drawings.

Described below are systems and methods for biomanufacturing. In some variation the systems and methods may be applied for cultivating tissue. In some variations the systems and methods may be applied in tissue regenerative therapies for injury and disease, physical enhancement, production of secreted products (e.g., biologic drugs), assay platforms (e.g., drug testing), ex vivo production of consumer goods such as textiles (e.g., leather), foods (e.g., meat), products secreted from the tissue (e.g., milk proteins, egg proteins, immunoglobulin, albumin, peptide growth factors, small molecules), tissue harvest (e.g., biological machinery & physical augmentation, plastic surgery) and machinery (e.g., biological actuators & motors), and/or the like. In some variation the systems and methods may be applied in cell spheroid cultivation, biofabrication, cultivation on tangentially-perfused surfaces, packed-bed bioreactors, and/or hollow-fiber bioreactors.

The systems and methods described in this disclosure have many advantages, such as enhanced tissue anchorage and retention, pressure gating mechanisms, and a conduit network for orthogonal diffusion of growing tissues. The systems and methods described herein may provide a novel platform-based methodology that may overcome the limitations occurring in biomanufacturing processes entailing the production of tissues from metazoan cells. This is accomplished at least in part by balancing optimized tissue perfusion and tissue anchorage to the substrate with cultivation pressures in a cohesive and novel biological manufacturing process. Further, by dispensing of scaffolds for development of thick tissues, challenges concerning tissue adulteration which may devalue, or disqualify use of the harvested tissue yields for targeted applications, as added expense, process inconsistency and labor associated with their process application may be obviated. Cell growth, tissue assembly and maturation are achievable all with the same cultivation vessel. Taken together, the features direct the cultivation of thick tissues by addressing the limitations of archetypal modalities for cultivation of tissues.

As used in the present disclosure and the appended claims, the singular forms "a," "an" and "the" include plural references unless the content clearly dictates otherwise.

Throughout the present disclosure and the appended claims, unless the context requires otherwise, the word "comprise," or variations such as "comprises" or "comprising," will be understood to imply the inclusion of a stated element or group of elements but not the exclusion of any other element or group of elements.

Cell-Based Meat

The cell-based meat products of the disclosure are produced by the in vitro culturing of naturally occurring, genetically engineered, or modified animal cells in culture.

The methods provided herein are applicable to any metazoan cell in culture. Generally, the cells are from any metazoan species whose tissues are suitable for dietary consumption. In some variations the cells may demonstrate a capacity for differentiation into mature tissue, such as skeletal muscle tissue, other muscle tissues, or any cell, cellular biomass, and/or tissue that can be consumed as cell-based meat or nutrients thereof. The cells in the present disclosure may be primary cells, or cell lines. The cells may be adherent-cells or non-adherent cells.

In some variations, the cells are derived from any non-human animal species intended for human or non-human dietary consumption (e.g. cells of avian, ovine, caprine, porcine, bovine, piscine origin) (e.g. cells of livestock, poultry, avian, game, or aquatic species, etc.).

In some variations, the cells are from livestock such as domestic cattle, pigs, sheep, goats, camels, water buffalo, rabbits and the like. In some variations, the cells are from poultry such as domestic chicken, turkeys, ducks, geese, pigeons and the like. In some variations, the cells are from game species such as wild deer, gallinaceous fowl, waterfowl, hare and the like. In some variations, the cells are from aquatic species or semi-aquatic species harvested commercially from wild fisheries or aquaculture operations, or for sport, including certain fish, crustaceans, mollusks, cephalopods, cetaceans, crocodilians, turtles, frogs and the like.

In some variations, the cells are from exotic, conserved or extinct animal species. In some variations, the cells are from *Gallus gallus, Gallus domesticus, Bos taurus, Sous scrofa, Meleagris gallopavo, Anas* platyrynchos, *Salmo salar, Thunnus thynnus, Ovis aries, Coturnix coturnix, Capra aegagrus hircus,* or *Homarus americanus.* Accordingly, exemplary cell-based meat products of the disclosure include avian meat products, chicken meat products, duck meat products, and bovine meat products.

In some variations, the cells are primary stem cells, self-renewing stem cells, embryonic stem cells, pluripotent stem cells, induced pluripotent stem cells, or differentiated progeny of pluripotent stem cells.

In some variations, the cells are modifiable by a genetic switch to induce rapid and efficient conversion of the cells to skeletal muscle tissue, connective tissue, fat tissue, and/or any other mature tissue for cultured meat production.

In some variations, the cells are myogenic cells, programmed to become muscle, or muscle-like cells. In some variations, the myogenic cells are natively myogenic, e.g. myoblasts. Natively myogenic cells include, but are not limited to, myoblasts, myocytes, satellite cells, reserve cells, side population cells, muscle derived stem cells, mesenchymal stem cells, myogenic pericytes, or mesoangioblasts.

In some variations, cells are of the skeletal muscle lineage. Cells of the skeletal muscle lineage include myoblasts, myocytes, and skeletal muscle progenitor cells, also called myogenic progenitors that include satellite cells, reserve cells, side population cells, muscle derived stem cells, mesenchymal stem cells, myogenic pericytes, and mesoangioblasts.

In other variations, the cells are not natively myogenic (e.g. are non-myogenic cells such as fibroblasts or non-myogenic stem cells that are cultured to become myogenic cells in the cultivation infrastructure).

In some variations, the cells of the cellular biomass are somatic cells. In some variations, the cells of the cellular biomass are not somatic cells.

In some variations the cells are genetically edited, modified, or adapted to grow without the need of specific ingredients including specific amino acids, carbohydrates, vitamins, inorganic salts, trace metals, TCA cycle intermediates, lipids, fatty acids, supplementary compounds, growth factors, adhesion proteins and recombinant proteins.

In some variations, the cells may comprise any combinations of the modifications described herein.

The cell-based meat of the present disclosure, generated using the cell media formulations provided herein, is suitable for both human and non-human consumption. In some variations, the cell-based meat is suitable for consumption by non-human animals, such as domesticated animals. Accordingly, the cell media formulations provided herein support the growth of "pet food", e.g. dog food, cat food, and the like.

In some variations the systems and methods may enable production of thick tissues without the need for an added internal scaffold to support tissue dimensionality.

In some variation the systems and methods may be applied for, but not limited to, cultivations of cell spheroids, biofabrication, cultivation on tangentially-perfused surfaces, packed-bed bioreactors and hollow-fiber bioreactors.

Systems for Cultivating Tissue

Described below are systems for cultivating tissue which may include a bioreactor, and a porous substrate arranged in the bioreactor, the porous substrate comprising at least one conduit extending between a first surface of the substrate and a second surface of the substrate opposite the first surface.

In some embodiments, the first surface is the surface that initially contacts the fluid and through which the fluid enters the porous substrate. The fluid may then flow through the porous substrate to reach the second surface. The fluid may exit the substrate from the second surface.

In some embodiments, the second surface is the surface that initially contacts the fluid and through which the fluid enters the porous substrate. The fluid may then flow through the porous substrate to reach the first surface. The fluid may exit the substrate from the first surface.

In some embodiments, cells and/or tissues are cultivated on the first surface of the substrate. In some embodiments, cells and/or tissues are cultivated on the second surface of the substrate. In some embodiments, cells and/or tissue are cultivated on both the first surface and the second surface of the substrate.

For example, generally, as shown in FIG. 1A, a system 100 for cultivating tissue may comprise a bioreactor 110 containing a substrate 120, an inlet 112, and an outlet 114. In some variations the inlet 112 may be in fluidic communication with a fluidic control system 130, and the fluidic control system 130 may further be connected to a vessel 140.

The bioreactor 110 may include an enclosure (e.g., a vessel or chamber) configured to provide a chamber suitable to allow for growth (e.g., sterile growth) of a meat product. The enclosure may include at least one inlet 112 configured to receive fluid, and at least one outlet 114 configured to output the fluid. The bioreactor 110 may provide a chamber of any suitable volume to allow for growth of the meat product. For example, the bioreactor 110 may include an internal volume of at least 1 L, between about 1 L and about 25 L, between about 25 L and about 200 L, between about 100 L and about 500 L, between about 500 L and about 1000 L, and between about 100 L and about 4000 L, between 4000 L and 100000 L including all values and sub-ranges in between. As described in further detail herein, one or more substrates may be housed or otherwise arranged within the bioreactor. In some variations, the bioreactor 110 may include one or more fluid diffusers to help distribute a fluid (e.g., cell culture media) over the substrate, such as in a predetermined fluid flow pattern. The fluid diffuser may, for example, help distribute fluid entering the bioreactor through the inlet(s) 112 in a generally uniform manner over the one or more substrates in the bioreactor. In some variations, the bioreactor 110 and associated components may be similar to those described in U.S. Patent Application No. 62/938,087, which is incorporated herein in its entirety by this reference.

The substrate 120 may be housed within the bioreactor 110. In some variations the substrate is a porous substrate (e.g., at least a portion of the substrate is porous). As described below, porous substrates may comprise a first surface and a second surface opposite the first surface. The first and second surface may be connected by at least one conduit. In some variations, the first surface 124 of the substrate 120 may face inlet 112, and the second surface 126 of the substrate may face outlet 114.

The fluidic control system 130 may permit precise control and modulation of various physical parameters, such as flow rate and pressure of fluid, to enable optimal cultivation of tissue in the bioreactor 110. In some variations, the fluidic control system 130 may additionally or alternatively be configured to control aspects of fluid flow between or among multiple bioreactors 110 connected as part of a fluidic system. In some variations the fluidic control system 130 may comprise suitable components such as pumps (e.g., peristaltic pumps), restriction points, valves, pressure and flow rate sensors, or combinations thereof. In some variations the fluidic control system may be between the vessel 140 and the bioreactor 110. In some variations the fluidic control system is downstream of or may follow the outlet 114.

The vessel 140 may be used to store any substance to be fed into bioreactor 110. For example, the vessel may contain fluids, such as nutrients, buffers, sterile water, enzyme solutions, or any other liquids applicable in cell culture medium and the cultivation process. In some variations the vessel 140 may be in fluidic communication with the bioreactor 110. In some variations the vessel 140 may contain gases, such as oxygen, carbon dioxide, nitrogen, argon, or any other gas applicable in cell culture. In some variations the vessel 140 may contain cells suspended in cell culture medium. In some variations the vessel 140 may contain contractile stimuli, such as small molecules, calcium channel modulators, or acetylcholine suspended in cell culture medium.

Substrates

The systems described in this disclosure comprise at least one substrate. In some variations the substrate is a porous substrate. Porous substrates may comprise a first surface and a second surface opposite the first surface. The first and second surface may be connected by at least one conduit. In some variations at least a portion of the porous substrates may be open, comprising continuous void volumes within a substrate that link to form tortuous conduits through the substrate from one surface to the other. In other variations at least a portion of the porous substrates may be closed, wherein void volumes exist but these volumes are not linked, and therefore do not provide tortuous conduits through the substrate.

Figure 1B:
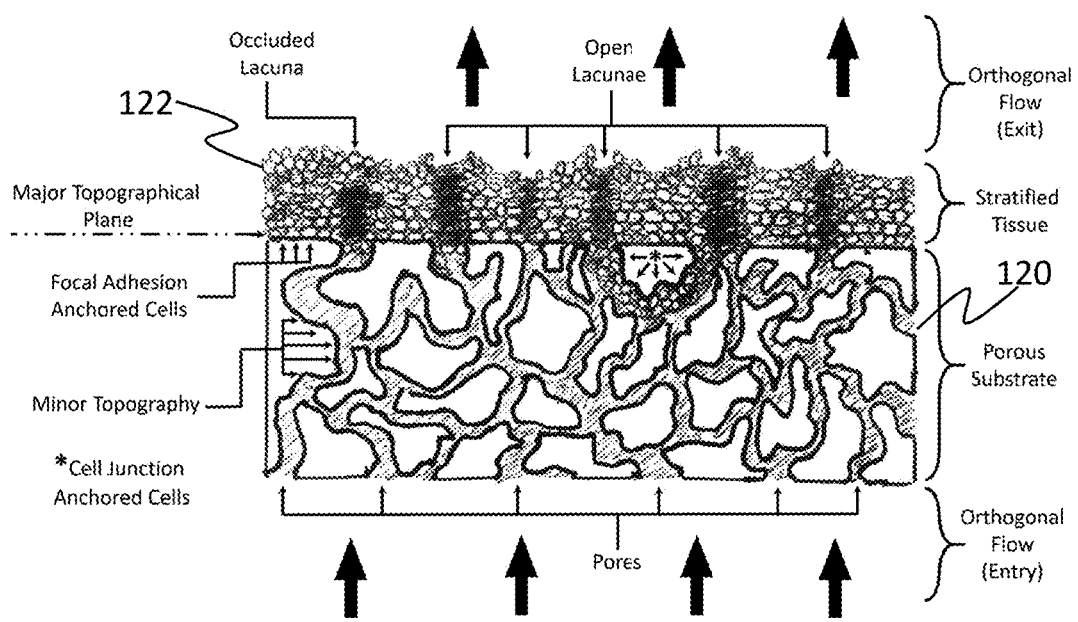
FIG. 1B depicts an illustrative schematic of an exemplary porous substrate for cultivating tissue with perfusion by orthogonal flow.

FIG. 1B shows schematic of an example of an open porous substrate 120 that may be used in a system for cultivation of tissue 122. Tissue for cultivation is cultured on at least a second surface 126 at the major topographical plane. A second surface 126 is opposite the first surface 124 and is connected to the first surface via one or more tortuous conduits. The porous substrate may be orthogonally perfused with fluids, such as cell culture medium, in the direction shown by the arrows in FIG. 1B. The fluid enters the tortuous conduits at the first surface 124 and flows towards the second surface 126 upon which cells and or tissues may be growing. Depending on fluid dynamics, upon reaching the second surface 126, the fluid may get blocked by the overlying layers of cells or stratified tissue (occluded lacuna) or exit through an open lacuna. If the lacuna is occluded, a pressure differential may accumulate at the site, which may potentially rupture the overgrowth and reopen the lacuna. The cells may grow on the surface and/or within the tortuous conduits. As shown in FIG. 1B, cells may attach or anchor to the substrate directly via focal adhesions and/or indirectly via cell-cell attachments. As described below, porous substrates with orthogonal perfusion have several advantages which enable high yield of thick tissues. Process consistency is simplified where the major topographical surface of a porous substrate is seeded and perfused versus the highly tortuous network of a carrier scaffold of a packed bed bioreactor, enabling even seeding distribution, and consistent laminar perfusion of cell culture medium. Cells and/or tissues may be cultivated on the first surface, second surface, or both the first surface and second surface of the substrate.

In some variations the substrate may have major topographical features that are, either alone or in combination, planar, concave or convex. In some variations the substrate may have a minor topographical feature, such as an open porous structure.

The porous substrate may be composed of any material appropriate for tissue culture. In some variations the porous substrate may be comprised of silicate, ceramic, carbon allotrope, metal, metallic alloy, synthetic polymer, biological polymer, synthetically-modified biological polymer, composite, or resin. In some variations the porous substrate may be comprised of stainless steel.

The porous substrate may be composed of any architecture appropriate for tissue culture. For example, in some variations at least a portion of the porous substrate architecture may be continuous, a gradient, granular, fibrous, spun, woven, stratified, fritted, sintered, bored, channeled, polygonal, spheroid, inverse spheroid, bifurcated between primary and secondary structures, linear, tortuous, periodic, patterned or stochastic, or any suitable combination thereof.

Figure 1C:
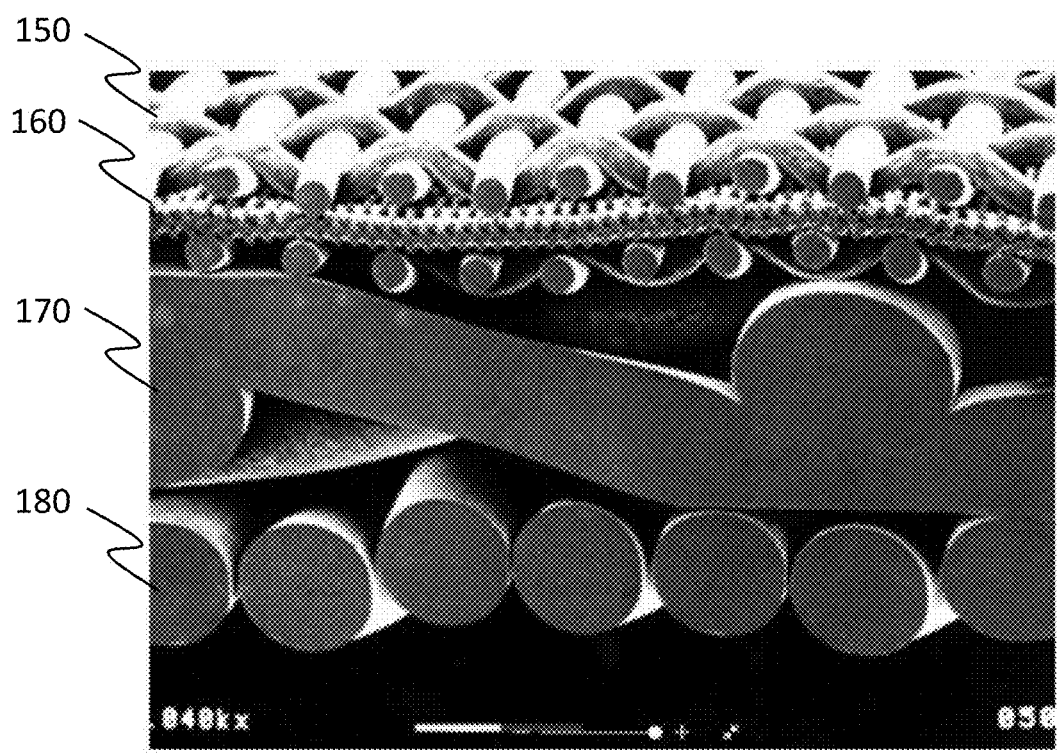
FIG. 1C depicts an exemplary porous substrate for cultivating tissue comprising a stainless steel sintered wire in layered mesh form.

In some variations the substrate may be a stainless steel sintered wire substrate. The stainless steel sintered wire substrate may be of different architectures as described above. In some variations the stainless steel sintered wire substrate may be in the form of a layered mesh. An example of a stainless steel sintered wire substrate is shown in FIG. 1C, comprising layers 150, 160, 170 and 180. Layers 150, 170 and 180 are structural components that provide rigidity to the mesh, while layer 160 determines that threshold pore size for the mesh. Various combinations of the layers may be employed. In some variations, the porous substrates may comprise only layer 160 and no structural layers, such as cloth-like substrates. In other variations the porous substrate may comprise of layer 160 and structural layers 170 and 180 only. In some variations the substrate may be comprised of sintered stainless steel granules, such as the 316LSS sintered powder porous metal Mott Discs available from Mott Corporation, Farmington, Connecticut, USA. In some variations the substrate may be comprised of sintered stainless steel layered, non-woven fibers.

The porous substrate may include any of various suitable dimensions. For example, in some variations the porous substrate may comprise a thickness (e.g., a mean axial thickness) of between about 25 μm-50 μm, 50 μm-100 μm, 100 μm-200 μm, 200 μm-400 μm, 400 μm-800 μm, 800 μm-1600 μm, 1.6 mm-3.2 mm, 3.2 mm-6.4 mm, 6.4 mm-12.8 mm, 1.28 cm-2.56 cm, or 2.56 cm-5.12 cm.

Additionally or alternatively, in some variations the porous substrate may include a width or diameter (e.g., a major axis constituting the mean radius perpendicular to the thickness designated as the minor axis) of between about 0.5 mm-1.0 mm, 1.0 mm-2.0 mm, 2.0 mm-4.0 mm, 4.0 mm-8.0 mm, 0.8 cm-1.6 cm, 1.6 cm-3.2 cm, 3.2 cm-6.4 cm, 6.4 cm-12.8 cm, 12.8 cm-25.6 cm, 25.6 cm-51.2 cm, 0.5 m-1.0 m, 1 m-2 m, 2 m-4 m, 4 m-8 m, 8 m-16 m, 16 m-32 m, or 32 m-64 m, or any suitable dimension.

The porous substrate may include any suitable pore size. For example, in some variations the mean substrate pore size is between about 0.01 nm-1 nm, 0.1 nm-0.5 nm, 0.5 nm-1 nm, 1 nm-5 nm, 5 nm-10 nm, 10 nm-20 nm, 20 nm-40 nm, 40 nm-80 nm, 80 nm-160 nm, 160 nm-320 nm, 320 nm-640 nm, 0.64 μm-1.2 μm, 1.2 μm-2.4 μm, 2.4 μm-4.8 μm, 4.8 μm-9.6 km, 9.6 μm-19.2 μm, 19.2 μm-38.4 μm, 38.4 μm-76.8 μm, 76.8 μm-153.6 μm, or 153.6 μm-307.2 μm, 307.2 μm-614.4 μm, or 0.6144 mm-1.2 mm, or any suitable pore size.

Furthermore, the porous substrate may include conduits of any suitable size (e.g., diameter) to permit passage of particulate matter therethrough. For example, in some variations the porous substrate may permit passage of particulates (e.g., cells) having up to a mean particulate diameter of between about 5 nm-10 nm, 10 nm-20 nm, 20 nm-40 nm, 40 nm-80 nm, 80 nm-160 nm, 160 nm-320 nm, 320 nm-640 nm, 0.64 μm-1.2 μm, 1.2 μm-2.4 μm, 2.4 μm-4.8 μm, 4.8 μm-9.6 μm, 9.6 μm-19.2 μm, 19.2 μm-38.4 μm, 38.4 μm-76.8 μm, 76.8 μm-153.6 μm, or 153.6 μm-307.2 μm, 307.2 μm-614.4 μm, or 0.61 mm-1.2 mm, or any suitable diameter.

Conversely, the porous substrate may include conduits of any suitable size (e.g., diameter) to restrict passage of particulate matter therethrough. For example, in some variations the porous substrate may restrict passage of particulates (e.g., cells) having up to a mean particulate diameter of between about 5 nm-10 nm, 10 nm-20 nm, 20 nm-40 nm, 40 nm-80 nm, 80 nm-160 nm, 160 nm-320 nm, 320 nm-640 nm, 0.64 μm-1.2 μm, 1.2 μm-2.4 μm, 2.4 μm-4.8 μm, 4.8 μm-9.6 μm, 9.6 μm-19.2 μm, 19.2 μm-38.4 μm, 38.4

μm-76.8 μm, 76.8 μm-153.6 μm, or 153.6 μm-307.2 μm, 307.2 μm-614.4 μm, or 0.61 mm-1.2 mm, or any suitable diameter.

The porous substrate may include any suitable porosity. For example, in some variations the porous substrate comprises apparent porosity (e.g. void volume) of about 0.1%-0.25%, 0.25%-0.50% 0.50%-1.0%, 1.0%-2.5%, 2.5%-5.0%, 5.0%-10%, 10%-20%, 20%-30%, 30%-40%, 40%-50%, 50%-60%, 60%-70%, 70%-80%, 80%-90%, 90%-95% or 95% to 99%.

Furthermore, the porous substrate may include a porous structure including conduits of any suitable tortuosity. For example, in some variations the porous substrate, the tortuosity of the open porous structure has a mean arc to chord-length ratio of between about 1.0-1.2, 1.2-1.4, 1.4-1.6, 1.6-1.8, 1.8-2.0, 2-3, 3-4,4-5, 5-6, 6-7,7-8, 8-9 or 9-10, or any suitable tortuosity.

In some variations the first surface of the substrate may be non-parallel to a flow direction associated with an inlet of the bioreactor. In some variations the first surface of the substrate may be oriented at an angle of between about 10 degrees and 170 degrees, 20 degrees and 160 degrees, about 30 degrees and 150 degrees, about 40 degrees and 140 degrees, about 50 degrees and 130 degrees, about 60 degrees and 120 degrees, about 70 degrees and 110 degrees, about 80 degrees and 100 degrees, or about 90 degrees relative to the flow direction associated with the inlet. In some variations the first surface of the substrate may be oriented at about 90 degrees relative to the flow direction associated with the inlet.

In some variations the first surface of the substrate may be non-parallel (e.g. orthogonal or perpendicular) to the flow direction associated with the inlet. Orthogonal flow through the substrate may impair contact inhibition of cell growth where perfused medium exits the pores and bypasses the tissue layer, thereby guiding autologous assembly of lacunae from the substrate by protracting porous occlusion through cell ingrowth, impairing contact inhibition of cell growth by proximal cells, and channeling nutrients and metabolic wastes, and possibly cells through developing tissues.

Furthermore, orthogonal flow may support tissue growth by stratification where cell motility is directed from one surface of the substrate to the other by one or more cell motility stimuli such as pressure differential, directional flow, gravitational vector, chemotaxis or electrotaxis through the substrate. In this variation, cells may be seeded onto and anchor to one side (for example, the first surface) of the substrate by adhesion. Subsequently, cells may be stimulated to migrate into the open porous structure by one or more cell motility stimuli. This migration may continue through one or more the tortuous conduits until the cells migrate to the opposite surface of the substrate and exit the porous structure while remaining adherent on a surface. Where cell growth had not occurred previously on the opposite side of the substrate, cell motility may continue from the open porous structure to the opposite side of the substrate (for example, the second surface). Where cell growth is already present on the opposite side of the substrate, cells exiting the open porous structure on the opposite side of the substrate may transition adherence from the open porous structure of the substrate to the cells, or their secreted products, on the opposite side of the substrate. Once transitioned, cell motility stimuli may direct further migration of cells to the apical cell layer on the opposite side of the substrate by means of lacunae. Where the aforementioned process for cell seeding onto an initial substrate surface through cell migration to the apical strata on the opposite side of the substrate is repeated in a semi-continuous or continuous manner, cell motility stimuli may be used to direct or enhance increased cell stratification into thick tissues. Where cell motility stimuli is used to direct or increase cell stratification, increased cell stratification may result in increased tissue thickness, as measured from the basal stratum of the tissue anchored to the porous substrate, to the apical stratum of the tissue.

In some variations the first surface of the substrate may be tangential to a flow direction associated with an inlet of the bioreactor. In some variations the first surface of the substrate may be parallel to a flow direction associated with an inlet of the bioreactor.

In some variations at least a portion of the substrate is non-porous. In some variations the substrate may be partially porous and partially non-porous. For example, at least a first section or segment of the substrate may be porous, while a second section or segment of the substrate may be non-porous. Furthermore, in some variations, different sections or segments of the substrate may be porous but have different pore sizes or diameters, porosity, tortuosity, etc.

Porous substrates described in this disclosure may have several advantages that enable high yields of tissue biomass. First, the use of porous substrates may allow for maximum cell anchorage, thereby minimizing, if not completely avoiding, premature tissue detachment due to inter- and/or intracellular contractile forces. The porous substrates may support direct or indirect adsorption of the cell's focal adhesion-anchorage motifs onto the substrate surface, biologically or synthetically derived, in a manner sufficiently robust to securely anchor cells and prevent unscheduled release of tissues. Compared to 2D substrate surfaces, porous substrates may provide larger surface area for cell growth and anchorage, for example by either open or closed porous structures smaller in diameter than the cell, but large enough to facilitate access and binding of cellular focal adhesion domains. Further, porous substrates may also augment cell anchorage indirectly via cell-cell attachment. For example, in substrates containing open porous features larger than the size of the cell, the entire cell can enter these substrates, and form junctions with cells around interconnected pores by cell-cell junctions, creating concentric linkages of tissues within the substrates and resulting in further augmented anchorage for tissues whose constituent cells are linked within the porous architecture (FIG. 1B). Thus, porous substrates may allow for direct and/or indirect interlinkage affording continuity, dimensionality and tensile strength to the cellular biomass.

The porosity distribution range or patterning may be modulated to determine the appropriate amount of tissue anchorage. If a threshold proportion of porous architecture is large enough to capacitate sufficient cell migration into the porous substrate, the substrate will become infiltrated with pervasive tissue development, rendering mechanical tissue removal from within the substrate difficult or impossible. Reciprocally, if a threshold proportion of the porous architecture is not sufficient to support focal adhesion and cell junction-dependent anchorage to the substrate, the level of anchorage may be insufficient to prevent release of tissues from the substrate during cytoskeletal contraction events. Accordingly, a continuum that exists between excessive and insufficient tissue anchorage may be modulated by the threshold proportion of porous architecture within the substrate. For applications in which harvest or recovery of tissue from the substrate is desired, the optimal amount of anchorage will support development and attachment of tissues throughout the cultivation cycle, enabling scheduled removal or release of the tissues at the time of harvest. The optimal porosity size, distribution range, and patterning may be varied in a cell-type and cultivation regimen-specific manner for specific tissue cultivation applications.

In some variations the pore size distribution range and patterning may permit a minor proportion of tissue integration into the substrate, such that the tissues integrated into the substrate may provide sufficient anchorage to help to prevent premature tissue release in the presence of cytoskeletal contraction and fluidic flow patterns, thereby increasing the tissue retention upon and harvestable yields from above the major surface topology. Because only a minor proportion of the cultivated tissue integrated into the substrate may be sufficient to support anchorage, harvest of the bulk tissue component from above the substrate's major topology remains unobstructed. Thus, compared to smooth substrates lacking porosity as featured in the tangentially-perfused surface cultivation modalities, which do not permit cell integration into the substrate where tissues are prone to release, and also compared to cultivation modalities featuring packed carrier scaffolding or hollow fibers, wherein tissues become integrated and cannot easily be extracted, the porous substrates as described in the present disclosure may enable enhanced tissue retention by cultivation threshold-specific pore size distribution range and patterning.

Another advantage of the porous substrates described in this disclosure is fluidic diffusion or perfusion through or between the first surface and second surface opposite the first surface of the substrate. Perfusion of fluids, such as cell culture medium, through a porous substrate may impede cellular occlusion of substrate porosity where such profusion is directed from the substrate and into the developing tissue. By averting porous occlusion, cellular confluence at the substrate's surface may be consequently prevented, thereby resulting in lacunae at sites of orthogonal perfusion. Extending from the pores directing orthogonal perfusion, nascent lacunae channel perfusion of the medium from the substrate pores to and through the tissue. Because cell to cell contact is interrupted at the site of lacunae, contact inhibition of cell growth within radii proximal to the lacunae may be impaired (FIG. 1B). Through inhibition of cell confluence at lacunae, contact inhibition of cell growth proximal to lacunae may initially be protracted or averted by fluidic shear from the substrate through the layer of growing cells.

Further, perfusion of cell medium allows for access to nutrients and clearance of accumulated metabolic wastes, without which tissues cease to grow and/or may become necrotic. Integration of perfusion conduits within tissues during culture and evenly distributed lacunae thus may help channel nutrients and metabolic waste through the tissue, thereby supporting its growth and viability.

Yet another advantage of the porous substrates described in this disclosure is precise and modular control over fluidic pressure and pressure differentials across the substrates. By selecting from the fluidic pressure conditions described below, a wide array of pressures can be targeted at the porous substrate surface in sequence with pressures higher than, lower than, or the same as pressures targeted on the opposite surfaces of the substrate. Therefore, longitudinally sequential fluid pressures can be selected according to the biological response of the cultivated cells for optimized tissue cultivation performance. Applied alone or in conjunction with in-line ambient pressure regulation, pressure differentials generated by orthogonal flow from the pump head may compartmentalize fluid pressure upstream and downstream of the porous substrate, which may be normalized to a targeted pressure on both surfaces of the substrate directional flow coupled with pressure regulation by inline pressure valves downstream of the substrate. Though variance from initial pressures may occur in archetypal anchorage-dependent cell cultivation modalities, the systems as further described herein enable precise tuning of pressure for optimal cultivation performance.

System Configurations

Figure 2A:
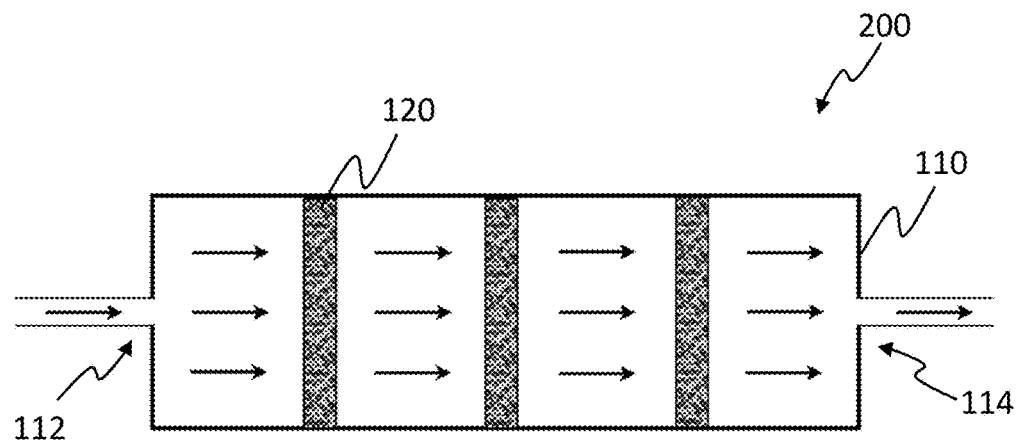
FIG. 2A depicts an illustrative schematic of a system for cultivating tissue comprising serially assembled substrates in the same bioreactor with perfusion by orthogonal flow.

One or more substrates may be arranged in any configuration within one or more bioreactors. For example, as shown in FIG. 1A, one single substrate may be arranged in a single bioreactor 110. As another example, in some variations, such as the configuration 200 shown in FIG. 2A, multiple substrates may be arranged in a single bioreactor. Serial assemblies may, for example, provide compact cultivation volume per unit surface area of the cultivation substrate, enabling increased scale of production. Moreover, serial assembly of substrates can provide multiple seeding configurations in substrate-delimited adjacent compartments, providing customizable utility for biological manufacturing applications. Although the bioreactor 110 shown in FIG. 2A houses three substrates 120 arranged in series, it should be understood that any suitable number (e.g., two, three, four, five, six, seven, eight, nine, ten, or more than ten) substrates may be arranged in a bioreactor 110. Furthermore, while the multiple substrates 120 are shown in FIG. 2A as arranged in series within the bioreactor 110, multiple substrates may be arranged in series, in parallel, or both. In other words, in some variations the system may include substrates assembled in parallel, facilitating sequential diffusion and/or flow of the culture medium and secreted products of cellular metabolism across substrates from one substrate to the next. Additionally or alternatively, in some variations the system may include substrates assembled in series, facilitating sequential diffusion and/or flow of the culture medium and secreted products of cellular metabolism across substrates from one substrate to the next.

Figure 2B:
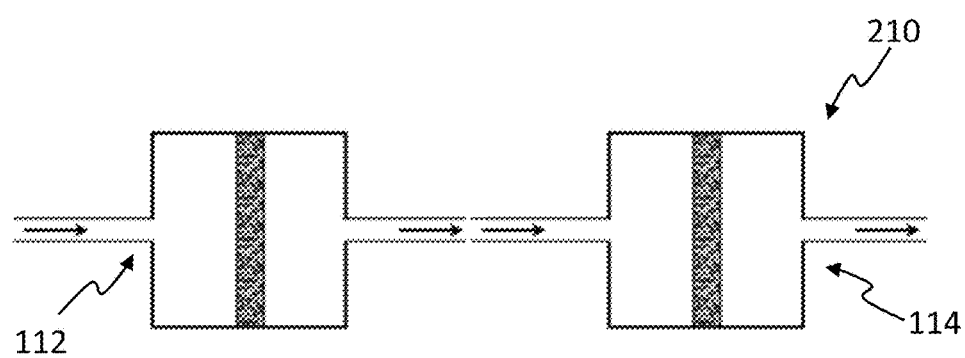
FIG. 2B depicts an illustrative schematic of a system for cultivating tissue comprising multiple bioreactors in series with perfusion by orthogonal flow.
Figure 2C:
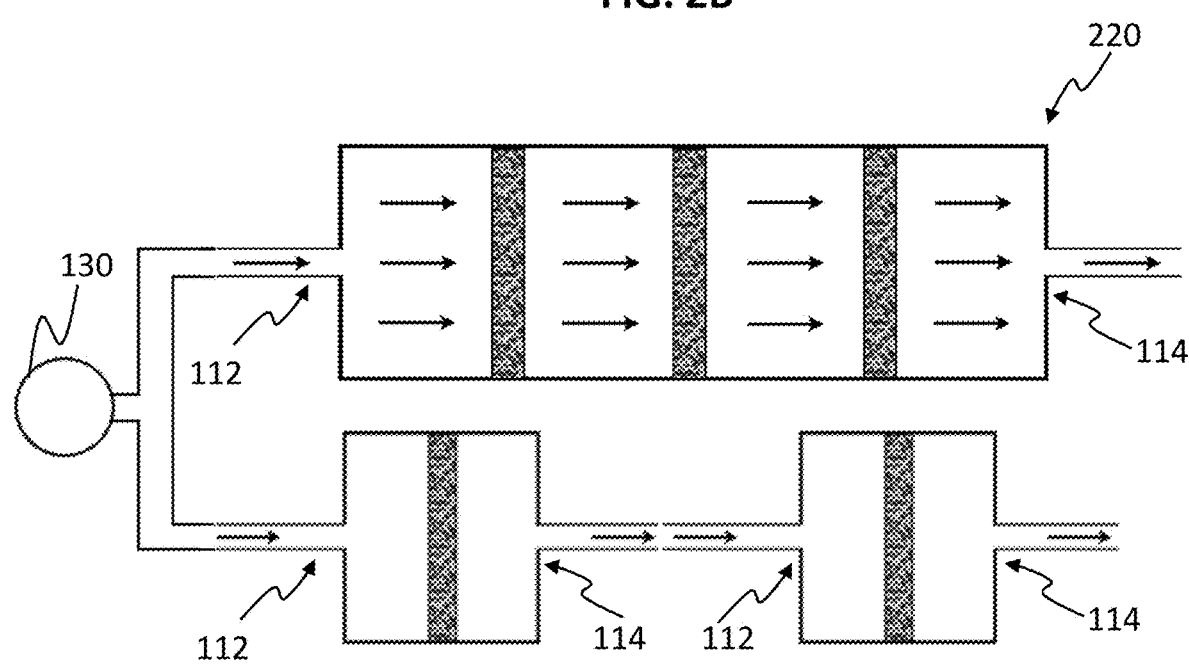
FIG. 2C depicts an illustrative schematic of a system for cultivating tissue multiple bioreactors in parallel with perfusion by orthogonal flow.

Furthermore, multiple bioreactors may be fluidically connected in any suitable configuration. For example, in some variations multiple bioreactors containing one or more substrates may be connected in series as shown in the configuration 210 shown in FIG. 2B. As another example, in some variations, multiple bioreactors containing one or more substrates may be connected in parallel as shown in the configuration 220 shown in FIG. 2C.

Methods for Cultivating Tissue

Figure 4:
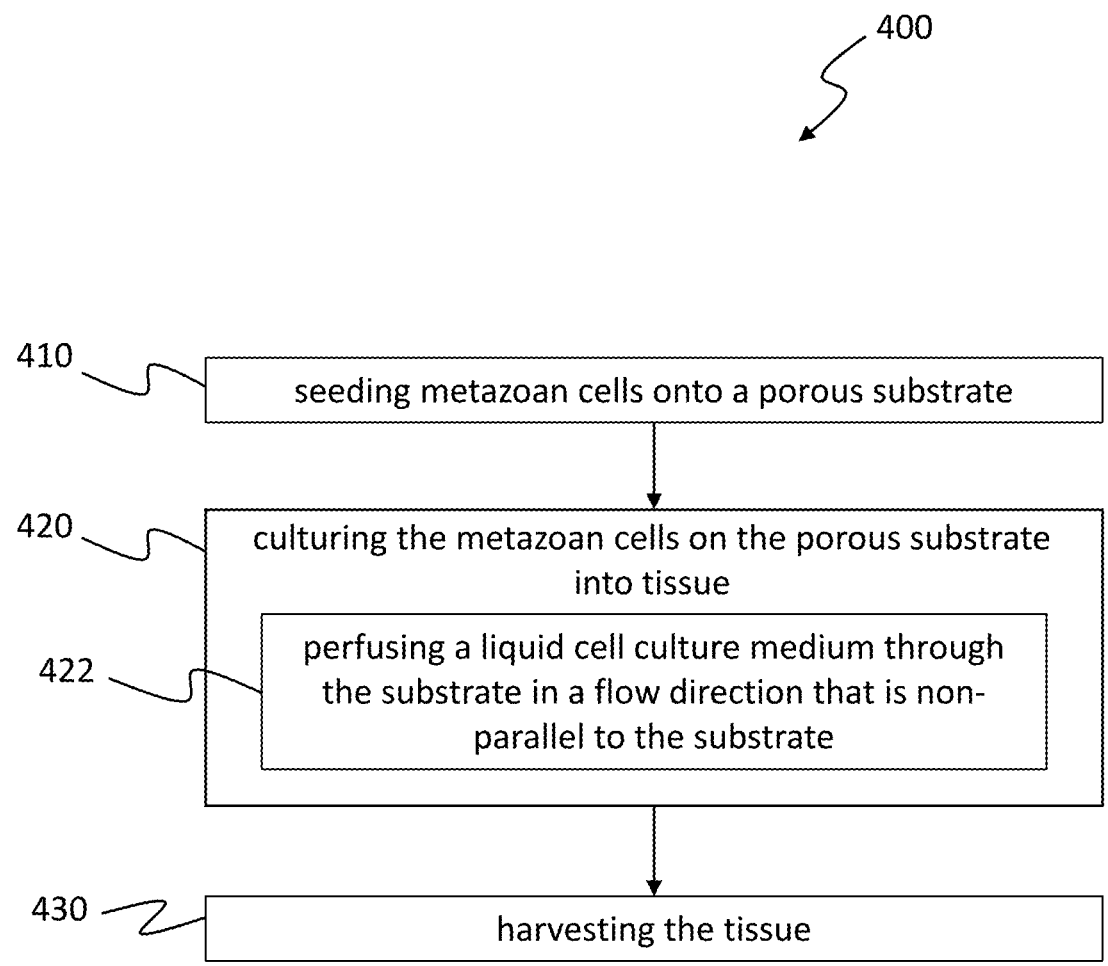
FIG. 4 depicts an illustrative flowchart of a method for cultivating tissue.

Described below are methods for cultivating tissue. In some variations, as shown in FIG. 4, a method 400 for cultivating tissue may include seeding metazoan cells onto a porous substrate 410, wherein the porous substrate may comprise at least one conduit extending between a first surface of the substrate and a second surface of the substrate opposite the first surface, culturing the metazoan cells on the porous substrate into tissue 420, wherein a liquid cell culture medium may be perfused through the substrate in a flow direction that is non-parallel (e.g. orthogonal, perpendicular) to the substrate 422, and harvesting the tissue 430 (FIG. 4). The methods described herein may be performed using any of the systems described above (e.g., using a porous substrate similar to that described above).

Seeding Cells

Cells may be seeded on the substrate by a variety of different methods. In some variations of the method cells may be seeded to an initial cell density on a substrate before installation of the substrate and cultivation of the cells within a bioreactor. In other variations a substrate devoid of cells may be placed within the bioreactor and seeded by flowing cells onto the substrate in the bioreactor via inlet 112

(FIG. 1A). In some variations of the method, cells may be seeded onto a substrate previously treated with focal-adhesion anchorage motifs, such as extracellular matrix proteins, or synthetic peptides, such as poly-D-lysine to facilitate cell anchorage.

In some variations of the method, more than one cell type may be seeded onto a first surface of the substrate. In some variations cells may be seeded on both a first and second surface of the substrate, where the second surface may be opposite the first surface. In some variations different cell types are seeded onto each surface of the substrate facilitating sequential diffusion and or flow of the culture medium and secreted products of cellular metabolism from one surface of the substrate to the other. Furthermore, the porous substrate may include conduits of any suitable size (e.g., diameter) to permit passage of particulate matter therethrough. For example, in some variations the porous substrate may permit passage of particulates (e.g., cells) having up to a mean particulate diameter of between about 5 nm-10 nm, 10 nm-20 nm, 20 nm-40 nm, 40 nm-80 nm, 80 nm-160 nm, 160 nm-320 nm, 320 nm-640 nm, 0.64 µm-1.2 µm, 1.2 µm-2.4 µm, 2.4 µm-4.8 µm, 4.8 µm-9.6 µm, 9.6 µm-19.2 µm, 19.2 µm-38.4 µm, 38.4 µm-76.8 µm, 76.8 µm 153.6 µm, or 153.6 µm-307.2 µm, 307.2 µm-614.4 µm, or 0.61 mm-1.2 mm, or any suitable diameter.

In some variations one cell type is seeded onto one surface of the substrate and more than one cell type is seeded onto the other surface of the substrate, facilitating diffusion and/or flow of the culture medium and secreted products of cellular metabolism from one surface of the substrate to the other. In some variations more than one cell type is seeded onto each surface of the substrate facilitating diffusion and/or flow of the culture medium and secreted products of cellular metabolism from one surface of the substrate to the other.

In some variations two different cell types may be seeded on the first and second surface of the substrate, respectively. Cultivation of tissues on opposite surfaces of the porous substrate may convey utility in cultivation applications where cell populations require separation. For example, one cell population, identified as the feeder population, may be required to provide support for another population cultivated as tissue for harvest, but is not suitable for incorporation into harvested tissues. Facilitated by the fluid dynamics regimen, this feeder cell population may provide secreted factors such as peptide hormones and extracellular matrix proteins supporting tissue development on the opposite surface of the substrate. For example, a fibrogenic cell population cultivated on one side of the substrate, such as fibroblasts may be used to supply collagen peptides to a non-fibrogenic cell population cultivated on the opposite site of the substrate, such as myoblasts, supporting their substrate anchorage, cell growth and tissue formation, without altering the cellular composition of the non-fibrogenic culture.

In some variations alternating flow may be applied for semi-continuous or continuous seeding applications. During cycles where flow is directed through an established tissue layer and into the substrate, suspended cells fed into the flow path may be flushed onto an extant tissue layer or through tissue lacunae into the porous architecture. Cells flushed onto the tissue layer may anchor to the existing tissue. Cells flushed into porous structures may be flushed out when the orthogonal flow cycle reverses. This continuous seeding approach can be used, for example, to assemble thick tissues independent of cell growth, and therefore, independent of contact inhibition of cell growth.

In some variations unidirectional flow may be applied for semi-continuous or continuous seeding applications. In such variations, unidirectional flow may direct motility of cells seeded on one side of the substrate into the substrate to egression from the other side of the substrate. Unidirectional egression subsequent to unidirectional flow may result in progressive accumulation of cells on the opposite side of the substrate to the seeded side supporting tissue growth and thickness.

Culturing Cells

In some variations of the method, metazoan cells may be seeded onto the substrate and cultured to increase number of anchorage-dependent cells, increase the mass of the cells, increase the extracellular biomass associated with the cells, increase the increase the tissue biomass associated with the anchored cells, or combinations thereof.

As described above, perfusion of the cell culture medium during cultivation provides many advantages for harvesting increased yield of thick tissue. Various properties of the fluid dynamics may be customized depending on the specific cultivation requirements. For instance, the cell culture medium may enter the bioreactor 110 via inlet 112 and contact the substrate 120 at any desired angle (FIG. 1A). In some variations the first surface of the substrate may be non-parallel (e.g. orthogonal, perpendicular) to a flow direction associated with an inlet of the bioreactor. In some variations the first surface of the substrate may be oriented at an angle of between about 10 degrees and 170 degrees, about 20 degrees and 160 degrees, about 30 degrees and 150 degrees, about 40 degrees and 140 degrees, about 50 degrees and 130 degrees, about 60 degrees and 120 degrees, about 70 degrees and 110 degrees, about 80 degrees and 100 degrees, or about 90 degrees to the flow direction associated with the inlet. In some variations the first surface of the substrate may be oriented at about 90 degrees to the flow direction associated with the inlet. In some variations the first surface of the substrate may be tangential to a flow direction associated with an inlet of the bioreactor. In some variations the first surface of the substrate may be parallel to a flow direction associated with an inlet of the bioreactor.

Orthogonal perfusion from the cell growth surface and into the substrate at the time of cell seeding for short durations (e.g., insufficient to cause extensive occlusion) may be strategically applied to improve cell seeding efficiency by increasing cell interaction with the substrate. For example, periodically alternating the direction of orthogonal flow through the substrate may enable attachment and cultivation of cells simultaneously on both surfaces of the substrate while reducing porous occlusion that otherwise would have occurred had perfusion been unidirectional. Additional nutrients may become accessible for tissue production if porous occlusion can be protracted or impaired through optimized flow regimens.

In some variations of the method, the liquid culture medium flow in the biomass milieu may be designated as static at a relatively low mean flow rate. For example, the liquid culture medium flow may be directed at a mean flow rate of less than about 2.5 nL/cm$^2$/minute generally perpendicular to the substrate's major topological features, or less than about 2.5 nL/cm$^2$/minute across the axial substrate thickness in any direction, or other suitable flow rate.

In some variations of the method, the mean media flow rate generally tangential to the substrate's major topological features may be between about 2.5 nL/cm$^2$/minute-5.0 nL/cm$^2$/minute, about 5.0 nL/cm$^2$/minute-7.5 nL/cm$^2$/minute, 7.5 nL/cm$^2$/minute-10 nL/cm$^2$/minute, 10 nL/cm$^2$/minute-25 nL/cm$^2$/minute, 25 nL/cm$^2$/minute-50 nL/cm$^2$/minute, 50 nL/cm²/minute-75 nL/cm²/minute, 75 nL/cm²/minute-100 nL/cm²/minute, 100 nL/cm²/minute-250 nL/cm²/minute, 250 nL/cm²/minute-500 nL/cm²/minute, 500 nL/cm²/minute-750 nL/cm²/minute, 750 nL/cm²/minute-1000 nL/cm²/minute, 1.00 μL/cm²/minute-1.25 L/cm²/minute, 1.25 μL/cm²/minute-1.50 μL/cm²/minute, 1.50 μL/cm²/minute-1.75 L/cm²/minute, 1.75 μL/cm²/minute-2.0 μL/cm²/minute, 2.0 μL/cm²/minute-2.5 μL/cm²/minute, 2.5 μL/cm²/minute-5.0 μL/cm²/minute, 5.0 μL/cm²/minute-7.5 μL/cm²/minute, 7.5 L/cm²/minute-10.0 μL/cm²/minute, 10.0 μL/cm²/minute-12.5 μL/cm²/minute, 12.5 L/cm²/minute-15.0 μL/cm²/minute, 15.0 μL/cm²/minute-17.5 μL/cm²/minute, 17.5 L/cm²/minute-20.0 μL/cm²/minute, 20 μL/cm²/minute-25 μL/cm²/minute, 25 μL/cm²/minute-50 μL/cm²/minute, 50 μL/cm²/minute-75 μL/cm²/minute, 75 μL/cm²/minute-100 μL/cm²/minute, 100 μL/cm²/minute-125 μL/cm²/minute, 125 μL/cm²/minute-150 μL/cm²/minute, 150 L/cm²/minute-175 μL/cm²/minute, 175 μL/cm²/minute-200 μL/cm²/minute, 200 μL/cm²/minute-250 μL/cm²/minute, 250 μL/cm²/minute-500 μL/cm²/minute, 500 μL/cm²/minute-750 L/cm²/minute, 750 μL/cm²/minute-1000 μL/cm²/minute, 1.00 mL/cm²/minute-1.25 mL/cm²/minute, 1.25 mL/cm²/minute-1.50 mL/cm²/minute, 1.50 mL/cm²/minute-1.75 mL/cm²/minute, 1.75 mL/cm²/minute-2.0 mL/cm²/minute, 2.0 mL/cm²/minute-2.5 mL/cm²/minute, 2.5 mL/cm²/minute-5.0 mL/cm²/minute, 5.0 mL/cm²/minute-7.5 mL/cm²/minute or 7.5 mL/cm²/minute-10.0 mL/cm²/minute, or any suitable flow rate or combination thereof.

In some variations the method may include perfusing liquid medium through the porous substrate and into the viable biomass of adherent cells in forward flow (e.g., in a first direction) at a rate of between about 2.5 nL/cm²/minute-5.0 nL/cm²/minute, 5.0 nL/cm²/minute-7.5 nL/cm²/minute, 7.5 nL/cm²/minute-10 nL/cm²/minute, 10 nL/cm²/minute-25 nL/cm²/minute, 25 nL/cm²/minute-50 nL/cm²/minute, 50 nL/cm²/minute-75 nL/cm²/minute, 75 nL/cm²/minute-100 nL/cm²/minute, 100 nL/cm²/minute-250 nL/cm²/minute, 250 nL/cm²/minute-500 nL/cm²/minute, 500 nL/cm²/minute-750 nL/cm²/minute, 750 nL/cm²/minute-1000 nL/cm²/minute, 1.00 μL/cm²/minute-1.25 μL/cm²/minute, 1.25 μL/cm²/minute-1.50 L/cm²/minute, 1.50 μL/cm²/minute-1.75 μL/cm²/minute, 1.75 μL/cm²/minute-2.0 L/cm²/minute, 2.0 μL/cm²/minute-2.5 μL/cm²/minute, 2.5 μL/cm²/minute-5.0 μL/cm²/minute, 5.0 μL/cm²/minute-7.5 μL/cm²/minute, 7.5 μL/cm²/minute-10.0 μL/cm²/minute, 10.0 L/cm²/minute-12.5 μL/cm²/minute, 12.5 μL/cm²/minute-15.0 μL/cm²/minute, 15.0 L/cm²/minute-17.5 μL/cm²/minute, 17.5 μL/cm²/minute-20.0 μL/cm²/minute, 20 μL/cm²/minute-25 μL/cm²/minute, 25 μL/cm²/minute-50 L/cm²/minute, 50 μL/cm²/minute-75 μL/cm²/minute, 75 μL/cm²/minute-100 μL/cm²/minute, 100 μL/cm²/minute-125 μL/cm²/minute, 125 L/cm²/minute-150 μL/cm²/minute, 150 μL/cm²/minute-175 μL/cm²/minute, 175 μL/cm²/minute-200 μL/cm²/minute, 200 μL/cm²/minute-250 μL/cm²/minute, 250 μL/cm²/minute-500 L/cm²/minute, 500 μL/cm²/minute-750 μL/cm²/minute, 750 μL/cm²/minute-1000 L/cm²/minute, 1.00 mL/cm²/minute-1.25 mL/cm²/minute, 1.25 mL/cm²/minute-1.50 mL/cm²/minute, 1.50 mL/cm²/minute-1.75 mL/cm²/minute, 1.75 mL/cm²/minute-2.0 mL/cm²/minute, 2.0 mL/cm²/minute-2.5 mL/cm²/minute, 2.5 mL/cm²/minute-5.0 mL/cm²/minute, 5.0 mL/cm²/minute-7.5 mL/cm²/minute, 7.5 mL/cm²/minute-10.0 mL/cm²/minute, 10 mL/cm²/minute-15 mL/cm²/minute, 15 mL/cm²/minute-20 mL/cm²/minute, 20 mL/cm²/minute-30 mL/cm²/minute, 30 mL/cm²/minute-45 mL/cm²/minute, or 45 mL/cm²/minute-60 mL/cm²/minute, or any suitable flow rate or combination thereof.

In some variations the method may include perfusing liquid medium from the viable biomass of adherent cells and through the porous substrate in reverse flow (e.g., in a second direction different (e.g., opposite) from the first direction) at a rate of between about 2.5 nL/cm²/minute-5.0 nL/cm²/minute, 5.0 nL/cm²/minute-7.5 nL/cm²/minute, 7.5 nL/cm²/minute-10 nL/cm²/minute, 10 nL/cm²/minute-25 nL/cm²/minute, 25 nL/cm²/minute-50 nL/cm²/minute, 50 nL/cm²/minute-75 nL/cm²/minute, 75 nL/cm²/minute-100 nL/cm²/minute, 100 nL/cm²/minute-250 nL/cm²/minute, 250 nL/cm²/minute-500 nL/cm²/minute, 500 nL/cm²/minute-750 nL nL/cm²/minute, 750 nL/cm²/minute-1000 nL/cm²/minute, 1.00 μL/cm²/minute-1.25 L/cm²/minute, 1.25 μL/cm²/minute-1.50 μL/cm²/minute, 1.50 μL/cm²/minute-1.75 L/cm²/minute, 1.75 μL/cm²/minute-2.0 μL/cm²/minute, 2.0 μL/cm²/minute-2.5 μL/cm²/minute, 2.5 μL/cm²/minute-5.0 μL/cm²/minute, 5.0 μL/cm²/minute-7.5 μL/cm²/minute, 7.5 L/cm²/minute-10.0 μL/cm²/minute, 10.0 μL/cm²/minute-12.5 μL/cm²/minute, 12.5 L/cm²/minute-15.0 μL/cm²/minute, 15.0 μL/cm²/minute-17.5 L/cm²/minute, 17.5 L/cm²/minute-20.0 μL/cm²/minute, 20 μL/cm²/minute-25 μL/cm²/minute, 25 μL/cm²/minute-50 μL/cm²/minute, 50 μL/cm²/minute-75 L/cm²/minute, 75 μL/cm²/minute-100 μL/cm²/minute, 100 μL/cm²/minute-125 μL/cm²/minute, 125 μL/cm²/minute-150 μL/cm²/minute, 150 L/cm²/minute-175 μL/cm²/minute, 175 μL/cm²/minute-200 L/cm²/minute, 200 μL/cm²/minute-250 μL/cm²/minute, 250 μL/cm²/minute-500 μL/cm²/minute, 500 μL/cm²/minute-750 L/cm²/minute, 750 μL/cm²/minute-1000 μL/cm²/minute, 1.00 mL/cm²/minute-1.25 mL/cm²/minute, 1.25 mL/cm²/minute-1.50 mL/cm²/minute, 1.50 mL/cm²/minute-1.75 mL/cm²/minute, 1.75 mL/cm²/minute-2.0 mL/cm²/minute, 2.0 mL/cm²/minute-2.5 mL/cm²/minute, 2.5 mL/cm²/minute-5.0 mL/cm²/minute, 5.0 mL/cm²/minute-7.5 mL/cm²/minute, 7.5 mL/cm²/minute-10.0 mL/cm²/minute, 10 mL/cm²/minute-15 mL/cm²/minute, 15 mL/cm²/minute-20 mL/cm²/minute, 20 mL/cm²/minute-30 mL/cm²/minute, 30 mL/cm²/minute-45 mL/cm²/minute, or 45 mL/cm²/minute-60 mL/cm²/minute, or other suitable flow rate or combination thereof.

In some variations the method may include perfusing liquid medium for a duration of one or more suitable flow intervals (e.g., flow duration in a particular direction (e.g., forward flow, reverse flow) and/or static flow). For example, a flow interval may include static or dynamic flow (e.g., forward flow or reverse flow) of between about 1 second-3 seconds, 3 seconds-10 seconds, 10 seconds-30 seconds, 30 seconds-60 seconds, 1 minute-3 minutes, 3 minutes-10 minutes, 10 minutes-30 minutes, 30 minutes-60 minutes, 1 hour-3 hours, 3 hours-8 hours, 8 hours-24 hours, 1 day-3 days, 3 days-7 days or 1 week-3 weeks, any suitable flow rate, or any combination thereof.

In some variations the method may include a primary sequence of flow intervals including [static flow→static flow], [forward flow→reverse flow], [static flow→reverse flow], [reverse flow→reverse flow], [reverse flow→static flow], [forward flow→forward flow], [forward flow→static flow], [reverse flow→forward flow], or [static flow→forward flow], or a suitable combination thereof.

In another variation the method may include a primary sequence of flow intervals including [static flow→static flow], [forward flow→forward flow], [forward flow→static flow], [tangential flow→tangential flow], [tangential flow→forward flow], [forward flow→tangential flow], [static flow→tangential flow], [static flow→forward flow], or [tangential flow→static flow], or a suitable combination thereof.

In another variation the method may include a primary sequence of flow intervals including [static flow→static flow], [static flow→reverse flow], [reverse flow→reverse flow], [reverse flow→static flow], [tangential flow→tangential flow], [tangential flow→reverse flow], [reverse flow→tangential flow], [static flow→tangential flow], [reverse flow→tangential flow], or [tangential flow→static flow] or a suitable combination thereof.

In another variation the method may include a primary sequence of flow intervals including [reverse flow→reverse flow], [reverse flow→static flow], [forward flow→reverse flow], [forward flow→forward flow], [forward flow→static flow], [tangential flow→tangential flow], [tangential flow→reverse flow], [reverse flow→tangential flow], [tangential flow→forward flow], [forward flow→tangential flow], [reverse flow→forward flow], [reverse flow→tangential flow], or [tangential flow→static flow] or a suitable combination thereof.

In yet another variation the method may include a primary sequence of flow intervals including [forward flow→reverse flow], [reverse flow→reverse flow], [forward flow→forward flow], or [reverse flow→forward flow] or a suitable combination thereof. In some variations of the method the primary sequence of flow intervals may be repeated to create a secondary sequence of primary sequence flow intervals. In contrast, the primary sequence of flow intervals may be followed by a primary sequence distinct from the first to create a discontinuous secondary sequence of primary flow intervals. As another example, the primary sequence flow interval duration may be repeated to create a secondary flow interval sequence equivalent to twice the duration (or other suitable multiple) of the primary sequence. In some variations the primary sequence flow interval duration may be followed by another sequence having a duration less than the first, resulting in a secondary sequence duration less than twice the duration of the first primary sequence. In other variations, primary sequence flow interval duration is followed by a primary sequence duration greater than the first, resulting in a secondary sequence duration greater than twice the duration of the first primary sequence.

In some variations of the method the secondary sequence of flow intervals is repeated to create a higher order (e.g., tertiary) sequences of flow intervals. In other variations the secondary sequence of flow intervals is followed by a secondary sequence distinct from the first to create a discontinuous higher-order sequence of flow intervals. In some variations the cultivation regimen may include a higher-order sequence of any suitable repetitious and or discontinuous sequence of secondary sequence flow intervals greater than the length of one secondary sequence flow interval, such as between about 1 to 2, 2 to 4, 4 to 8, 8 to 16, 16 to 32, 32 to 64, 64 to 128, 128 to 256, 256 to 512, 512 to 1028, 1028 to 2056, 4112 to 8224, 8224 to 16448, 16448 to 32896, 32896 to 65792, 65792 to 131584, or 131584 to 226800 sequential secondary sequences.

In some variations, the method may include perfusing liquid medium in any suitable combination of flow rates, flow intervals, and/or flow directions such as those described above. For example, in some variations, the perfusion flow pattern may be regular (e.g. continuous) or irregular (e.g. discontinuous) (e.g., regular or irregular patterns of flow rates, flow intervals, and/or flow directions). In some variations, at least a first portion of the perfusion flow pattern may be regular, while at least a second portion of the perfusion pattern may be irregular. Furthermore, some or all of the perfusion flow pattern may be preprogrammed (e.g., occurring in a predetermined manner), while some or all of the perfusion flow pattern may be random.

Figure 3A:
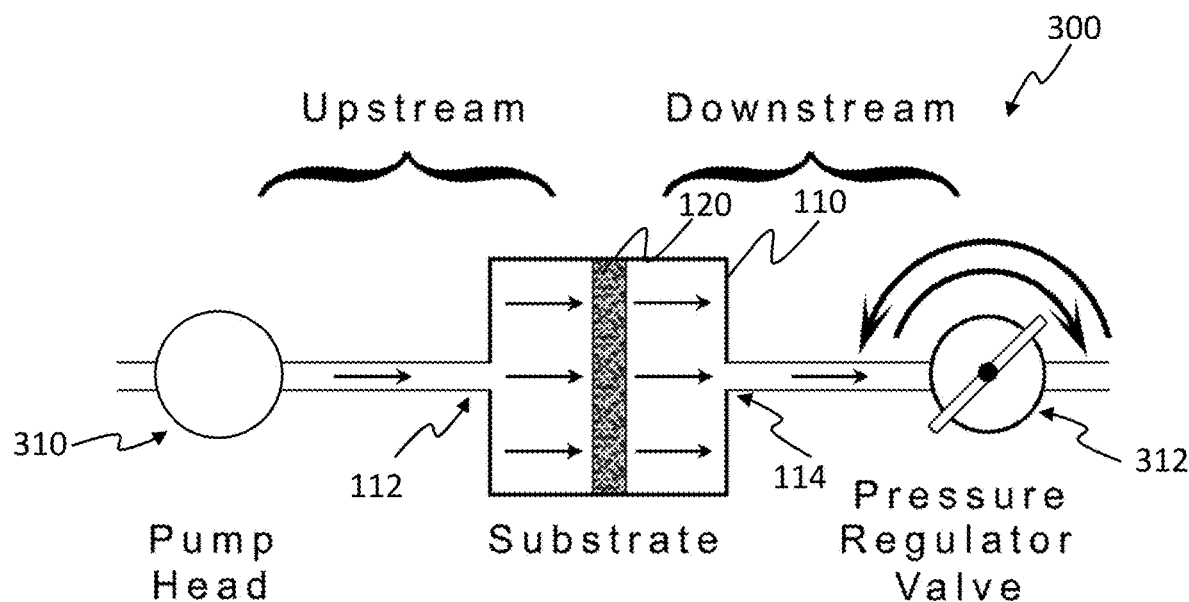
FIG. 3A depicts an illustrative schematic of a system for cultivating tissue comprising a bioreactor containing a substrate, with perfusion by orthogonal flow in a forward flow direction.

Orthogonal flow through porous substrates may result in a pressure differential across the substrate. The pressure differential may be the difference in fluid pressure prior to entering the porous substrate (upstream of the porous substrate), within the porous substrate and after exiting the porous substrate (downstream of the porous substrate). The magnitude of the pressure differential may be determined by factors influencing fluid dynamics through the substrate including but not limited to total flow rate, substrate tortuosity, and total open porosity volume within the substrate. Reduced flow rates, reduced substrate tortuosity, and increased open porous void volume each may serve to reduce the pressure differential. Conversely, increased flow rates, increased substrate tortuosity, and decreased open void volume each may serve to increase the pressure differential. In the absence of other partial flow barriers within the flow circuit housing the substrate, the fluid pressure entering the substrate may exceed the fluid pressure exiting the substrate where fluid flow rate is driven by an inline upstream pump head. In some variations the pump head 310 is upstream of the substrate 120 and pumping directionally onto the substrate, pressure accumulates between the pump head and the substrate creating a pressure differential across the substrate (FIG. 3A).

In some variations, achieving targeted pressures on either surface of the substrate may not be possible by modulating the flow rate, substrate tortuosity and void volume alone. Examples of such circumstances may include situations in which: (1) flow through the substrate is targeted but a pressure differential at the substrate is not; (2) a pressure differential at the substrate is not targeted and a pressure higher than the upstream pressure is targeted on both surfaces of the substrate; and (3) a downstream pressure is targeted less than the upstream pressure but greater that the ambient pressure. In some variations (e.g., in which a pressure differential across the substrate is not desired, or otherwise where more flow control is desirable), at least one flow regulator valve may be installed within the flow circuit, such as downstream of the substrate, and may be adjusted to restrict the flow equivalent to the flow restriction imparted within the flow path by the substrate, thereby moving the pressure differential from the substrate to the valve. Equivalent flow restriction is reached when under flow, the pressure upstream and downstream of the substrate are equivalent, thereby eliminating the pressure differential at the substrate. Additionally or alternatively (e.g., in variations in which, in addition to eliminating the pressure differential at the substrate, an increased pressure upstream and downstream pressure are both targeted) the downstream flow regulator valve may be adjusted further until the flow restriction imparted by the valve is greater than the flow restriction imparted by the substrate. Additionally or alternatively, (e.g., in variations in which an increased downstream pressure is targeted greater than the initial downstream pressure, but less than the upstream pressure), the downstream flow regulator valve may be adjusted until the flow restriction at the valve is less than the flow restriction imparted by the substrate, but greater than the initial downstream pressure.

Figure 3B:
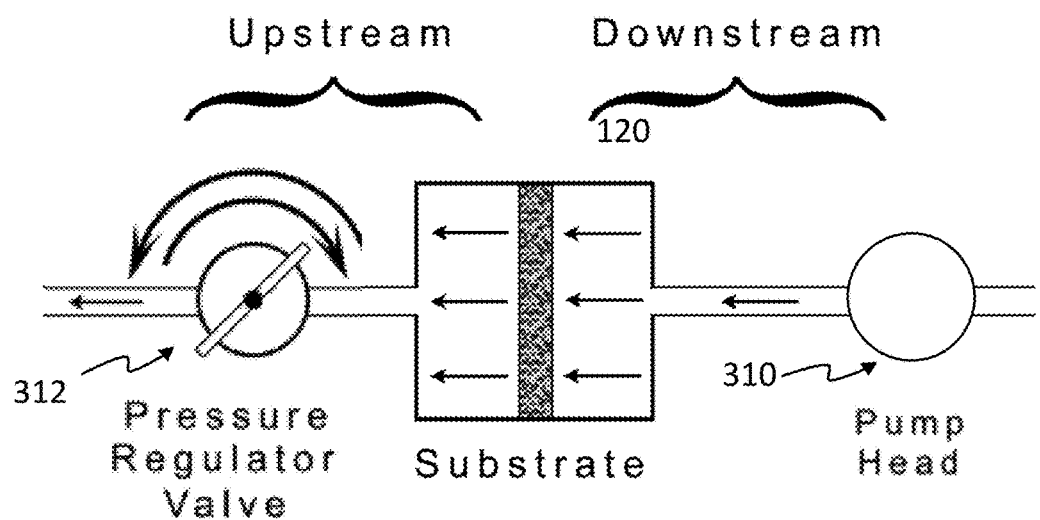
FIG. 3B depicts an illustrative schematic of a system for cultivating tissue comprising a bioreactor containing a substrate, with perfusion by orthogonal flow in a reverse flow direction.

In some variations, flow configurations may facilitate a system that targets upstream and/or downstream pressures lower than respective initial pressures. In such configurations, the pump head configuration pumps away from the substrate, creating a pressure drop between the pump head 310 and the substrate 120 while simultaneously reversing the pressure differential direction (FIG. 3B). Low pressure configurations targeted may be included where: (1) an upstream pressure lower than the downstream pressure is targeted with a pressure differential at the substrate; (2) lower upstream and downstream pressures are targeted without a pressure differential at the substrate; (3) upstream and downstream pressures are targeted without a pressure differential where the downstream pressure is equal to the upstream pressure, but less than the initial upstream pressure; and/or (4) a pressure differential is targeted where the upstream pressure is lower than the downstream pressure and the downstream pressure is lower than the initial downstream pressure.

Lower upstream pressure with a differential pressure at the substrate may be achieved by pumping fluid away from the substrate, in the absence of flow restrictions imparted by the downstream flow valve. While retaining upstream low pressure, the pressure differential across the substrate may be eliminated by adjusting the pressure regulator valve such that the flow restriction imparted by the valve is equivalent to the flow restriction imparted by the substrate. While retaining low pressure without a pressure differential, the upstream and downstream pressures may further be reduced by adjusting the pressure regulator valve such that the flow restriction imparted by the valve exceeds that of the flow restriction imparted by the substrate. If pressure differential is desired where the downstream pressure is less than the initial downstream pressure, and the upstream pressure is less than the downstream pressure, the pressure regulator valve may be adjusted so that flow restrictions imparted by the valve are less than flow restriction imparted by the substrate but greater than initial flow restrictions.

Using configurations such as those described above, the pressures at on one or both surfaces of the porous substrate may be any suitable pressure. For example, in some variations of the method the fluid pressure on at least one surface of the porous substrate may be between about 0.1 psi-0.25 psi, 0.25 psi-0.50 psi, 0.50 psi-0.75 psi, 0.75 psi-1.0 psi, 1.0 psi-1.5 psi, 1.5 psi-2.0 psi, 2.0 psi-3.0 psi, 3.0 psi-4.0 psi, 4 psi-5 psi, 5 psi-10 psi, 10 psi-14.7 psi, 14.7 psi-20 psi, 20 psi-30 psi, 30 psi-50 psi, 50 psi-100 psi, 100 psi-250 psi, 250 psi-500 psi, 500 psi-1000 psi, 1000 psi-2000 psi, 2000 psi-4000 psi, 4000 psi-8000 psi, or 8000 psi-16,000 psi during a flow interval.

In some variations of the method the fluid pressure differential across the porous substrate minor axis during the primary sequence interval is normalized on both surfaces of the substrate to about 0.1 psi-0.25 psi, 0.25 psi-0.50 psi, 0.50 psi-0.75 psi, 0.75 psi-1.0 psi, 1.0 psi-1.5 psi, 1.5 psi-2.0 psi, 2.0 psi-3.0 psi, 3.0 psi-4.0 psi, 4.0 psi-5.0 psi, 5.0 psi-6.0 psi, 6.0 psi-7.0 psi, 7.0 psi-8.0 psi, 8.0 psi-9.0 psi, 9.0 psi-10 psi, 10 psi-12 psi, 12 psi-14 psi, 14 psi-16 psi, 16 psi-18 psi, 18 psi-20 psi, 20 psi-24 psi, 24 psi-28 psi, 28 psi-32 psi, 32 psi-36 psi, 36 psi-40 psi, 40 psi-50 psi, 50 psi-60 psi, 60 psi-70 psi, 70 psi-80 psi, 80 psi-90 psi, 90 psi-100 psi, 100 psi-125 psi, 125 psi-150 psi, 150 psi-175 psi, 175 psi-200 psi, 200 psi-300 psi, 300 psi-400 psi, 400 psi-500 psi, 500 psi-600 psi, 600 psi-700 psi, 700 psi-800 psi, 800 psi-900 psi, 900 psi-1,000 psi, 1,000 psi-1,250 psi, 1,250 psi-1,500 psi, 1,500 psi-1,750 psi, 1,750 psi-2,000 psi, 2,000 psi-3,000 psi, 3,000 psi-4,000 psi, 4,000 psi-5,000 psi, 5,000 psi-6,000 psi, 6,000 psi-7,000 psi, 7000 psi-8,000 psi, 8,000 psi-9,000 psi, 9,000 psi-10,000 psi, 10,000 psi-12,000 psi, 12,000 psi-14,000 psi, or 14,000 psi-16,000 psi.

In some variations of the method the secondary sequence flow interval may be comprised of a primary sequence of repeated flow interval pressure differential or no pressure differential, where the extant pressure differential is less than 0.1 psi. In other variations the secondary sequence flow interval is comprised of a primary sequence of flow interval pressure differential that is followed by a primary sequence with no pressure differential, where the extant pressure differential is less than 0.1 psi. In other variations the secondary sequence flow interval is comprised of a primary sequence of flow intervals where there is no pressure differential, (where the extant pressure differential is less than 0.1 psi) followed by a primary sequence flow interval pressure where there is a pressure differential, (where the extant pressure differential is greater than 0.1 psi), where the primary sequence pressure of the first primary sequence flow interval is about equal to or greater than 0.1 psi less than the second primary sequence flow interval.

In some variations of the method, higher order (e.g. tertiary) sequence flow intervals alone or in repetition are comprised of differential pressure cycles or pressure cycles where there is no pressure differential (where the extant pressure differential is less than 0.1 psi) constituent to their secondary sequences. In other variations tertiary sequence flow intervals alone or in repetition are comprised of differential pressure cycles and pressure cycles where there is no pressure differential (where the extant pressure differential is less than 0.1 psi) constituent to their secondary sequences.

It should be understood that in some variations, pressure differentials (or absence thereof) across a substrate may be controlled in any suitable manner using the fluidic control system, including any combination of the above configurations and/or other suitable configurations. Furthermore, the fluidic control system may control fluid flow such that different substrates may have different pressure differentials.

Harvesting Tissue

As shown in FIG. 4, the method 400 may further include harvesting the tissue cultivated on the one or more porous substrates. Cultivated tissue may be accessible for harvest from the one or more substrates by any suitable methods such as mechanical removal, enzymatic dissociation, hyper-induction of cytoskeletal contraction or fluidic flush. The tissue may, for example, be harvested in bulk (e.g. as sheets) separable from the one or more substrates.

Accordingly, the systems and methods described herein may utilize porous substrates to increase harvestable yield of tissue.

In some variations the method for increasing tissue biomass (e.g., through culture of anchorage-dependent metazoan cells on a substrate with an open porous architecture) grown per unit of surface area of major topological substrate features may be between about 10%-20%, 20%-40%, 40%-80%, 80%-160%, 160%-320%, 320%-640%, 640%-1,280%, 1,280%-5,120%, 5,120%-10,240%, 10,240%-20,480%, 20,480%-40,960%, 40,960%-81,920%, 81,920%-163,840%, 163,840%-327,680%, or 327,680%-655,360% greater relative to that grown on a non-porous substrate of the same material.

In some variations the method for increasing tissue biomass grown per unit of surface area of major topological substrate features may be about 350 μg/cm$^2$-700 μg/cm$^2$, 0.7 mg/cm$^2$-1.4 mg/cm$^2$, 1.4 mg/cm$^2$-2.8 mg/cm$^2$, 2.8 mg/cm$^2$-5.6 mg/cm$^2$, 5.6 mg/cm$^2$-11.2 mg/cm$^2$, 11.2 mg/cm$^2$-22.4 mg/cm$^2$, 22.4 mg/cm$^2$-44.8 mg/cm$^2$, 44.8 mg/cm$^2$-89.6 mg/cm$^2$, 89.6 mg/cm$^2$-179.2 mg/cm$^2$, 179.2 mg/cm$^2$-358.4 mg/cm$^2$, 358.4 mg/cm$^2$-716.8 mg/cm$^2$, 0.7 g/cm$^2$-1.4 g/cm$^2$, 1.4 g/cm$^2$-2.8 g/cm$^2$, 2.8 g/cm$^2$-5.6 g/cm$^2$, 5.6 g/cm$^2$-11.2 g/cm$^2$, or 11.2 g/cm$^2$-22.4 g/cm$^2$ comprising the culture of anchorage-dependent metazoan cells onto a substrate whose major topographical features are, either alone or in combination, planar, concave or convex surfaces and whose minor topological features are an open porous structure.

In some variations the method for increasing tissue thickness grown from the major topological substrate features may result in a tissue thickness of about 10%-20%, 20%-40%, 40%-80%, 80%-160%, 160%-320%, 320%-640%, 640%-1,280%, 1,280%-5,120%, 5,120%-10,240%, 10,240%-20,480%, 20,480%-40,960%, 40,960%-81,920%, 81,920%-163,840%, or 163,840%-327,680%, or 327,680%-655,360% greater relative to that grown on a non-porous substrate of the same material, comprising of a culture of anchorage-dependent metazoan cells on a substrate whose major topographical features constitute, either alone or in combination, planar, concave or convex surfaces and whose minor topological features constitute an open porous structure.

In some variations the method for increasing the of tissues thickness grown from the major topological substrate features may result in tissues about 10 µm-20 µm, 20 µm-40 µm, 40 µm-80 µm, 80 µm-160 µm, 160 µm-320 µm, 320 µm-640 µm, 0.640 mm-1.28 mm, 1.28 mm-5.12 mm, 0.512 mm-1.02 mm, 1.02 cm-2.04 cm, 2.04 cm-4.08 cm, 4.08 cm-8.16 cm, 8.16 cm-16.32 cm, or 16.32 cm-32.64 cm, or 32.64 cm-65.28 cm thick, from the basal to apical strata, comprising of a culture of anchorage-dependent metazoan cells on a substrate whose major topographical features constitute, either alone or in combination, planar, concave or convex surfaces and whose minor topological features constitute an open porous structure.

In some variations the method for increasing the nutrient density of tissue grown per unit of surface area attached to major topological substrate features may result in a tissue thickness of about 10%-20%, 20%-30%, 30%-40%, 40%-50%, 50%-60%, 60%-70%, 70%-80%, 80%-90%, 90%-100%, 100%-120%, 120%-140%, 140%-160%, 160%-180%, 180%-200%, 200%-220%, 220%-240%, 240%-260%, 260%-280%, or 280%-300% greater relative to that grown on a non-porous substrate of the same material, comprising of a culture of anchorage-dependent metazoan cells on a substrate whose major topographical features constitute, either alone or in combination, planar, concave or convex surfaces and whose minor topological features constitute an open porous structure.

In some variations the method for increasing retention of viable biomass attached to a substrate may be increased by about 1 day-2 days, 2 days-3 days, 3 days-4 days, 4 days-5 days, 5 days-6 days, 6 days-7 days, 7 days-8 days, 8 days-9 days, 9 days-10 days, 10 days-11 days, 11 days-12 days, 12 days-13 days, 13 days-14 days, 14 days-16 days, 16 days-18 days, 18 days-20 days, 20 days-22 days, 22 days-24 days, 24 days-26 days, 26 days-28 days, 28 days-30 days, 30 days-34 days, 34 days-38 days, 38 days-42 days, 42 days-46 days, 46 days-50 days, 50 days-54 days, 54 days-58 days, or 58 days-62 days, relative to that grown on a non-porous substrate of the same material, comprising of a culture of anchorage-dependent metazoan cells on a substrate whose major topographical features constitute, either alone or in combination, planar, concave or convex surfaces and whose minor topological features constitute an open porous structure.

EXAMPLES

Example 1. Tissue Retention on Porous Substrates

To assess the relative retention of adherent cells and their derivative tissues to porous and non-porous substrates, chicken fibroblasts were seeded at a density of $2.0 \times 10^4$ cells/cm$^2$ on smooth 316L stainless steel (SS), tissue culture plastic surface (TCPS) and onto aluminum oxide ceramic substrates in a cell growth medium and cultured for up to 12 days in static culture conditions with partial culture medium changes every 2-3 days. SS and TCPS substrates used were non-porous whereas a ceramic substrates had porosity grades of <0.5, 4, 16, 40 and 100 µM. Cultures were imaged under a microscope at days 1, 4, 7 and 12 post-seeding using a Calcein AM fluorescent vital stain.

Figure 5A:
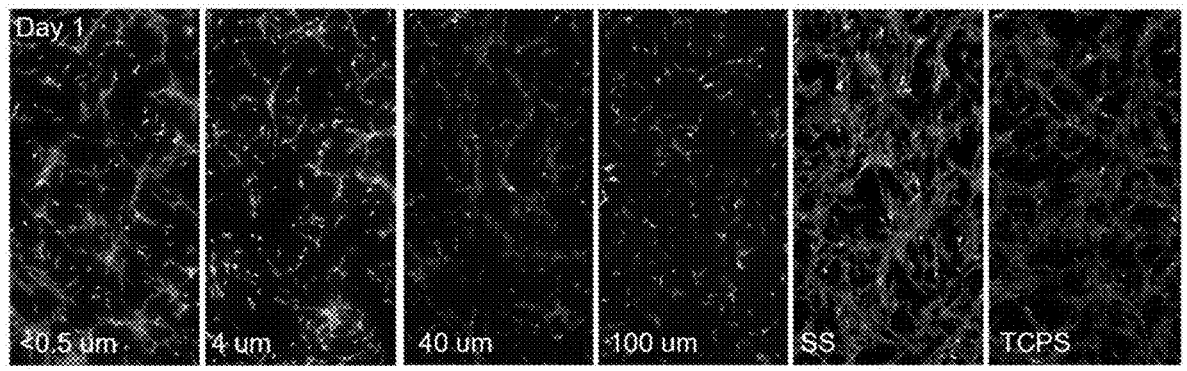
FIG. 5A depicts growth of chicken fibroblasts on ceramic substrates with porosity grades of <0.5, 4, 40 and 100 μm, in addition to non-porous substrates comprising stainless steel (SS) and tissue culture polystyrene (TCPS) at day 1.
Figure 5B:
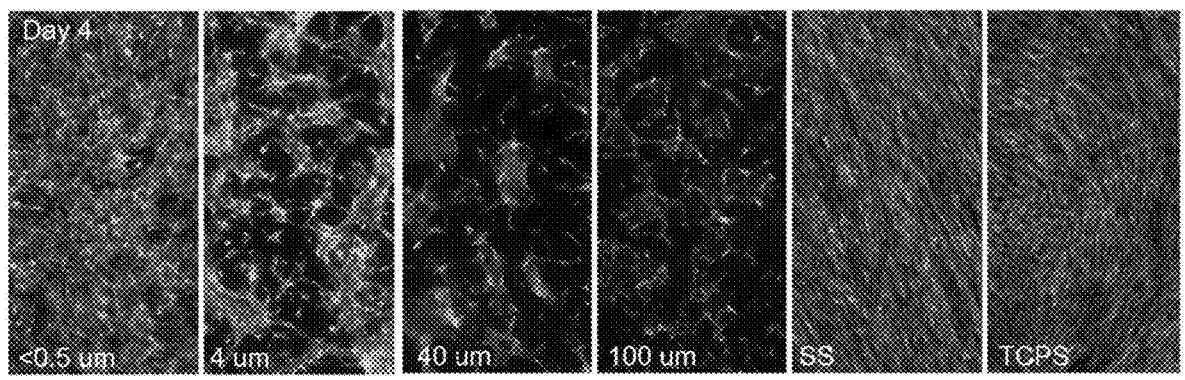
FIG. 5B depicts growth of chicken fibroblasts on ceramic substrates with porosity grades of <0.5, 4, 40 and 100 μm, in addition to non-porous substrates comprising stainless steel (SS) and tissue culture polystyrene (TCPS) at day 4.
Figure 5C:
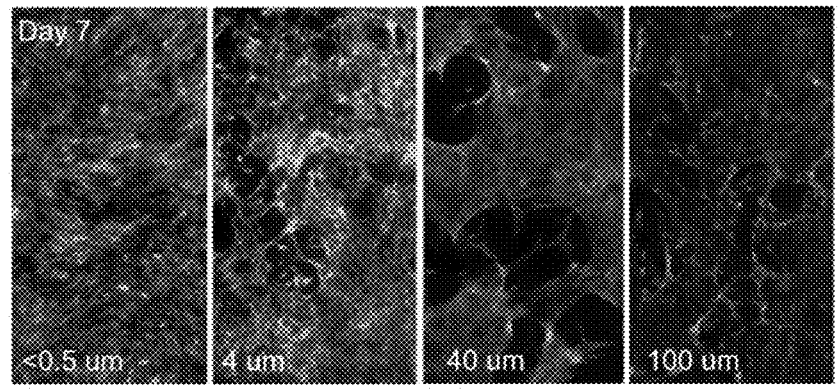
FIG. 5C depicts growth of chicken fibroblasts on ceramic substrates with porosity grades of <0.5, 4, 40 and 100 μm at day 7.
Figure 5D:
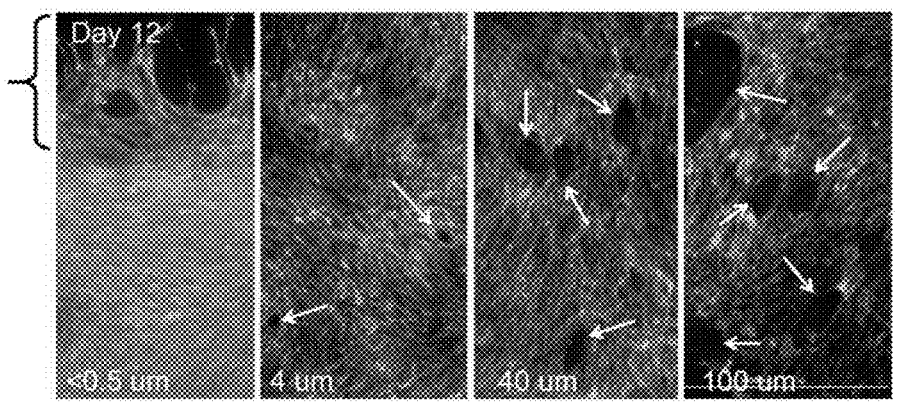
FIG. 5D depicts growth of chicken fibroblasts on ceramic substrates with porosity grades of <0.5, 4, 40 and 100 μm at day 12. The bracket demarcates the border of tissue release from the substrate on the <0.5 μm porosity grade substrates. Arrows demarcate lacunae within tissues cultivated on 4, 40, and 100 μm porosity grade substrates.

Day 1 Calcein AM staining revealed even seeding distribution and sub-confluent cell growth on all substrates, although the non-porous SS and TCPS substrates appeared to present a higher confluence than the porous ceramic substrates (FIG. 5A). By day 4, cell growth on the SS and TCPS substrates had reached confluence as cell growth presented on the <0.5 µm porous ceramic substrate approached confluence. Progressively less confluence was observed with increasing porosity presented by the 4, 40 and 100 µm porosity grade ceramics (FIG. 5B). By day 7, cells had begun to form tissues. Tissues from the non-porous SS and TCPS released from their substrate in an unscheduled manner (not shown) prior to day 7. In contrast, tissues observed on the porous substrates remained anchored. Cells had reached confluence on the ceramic substrate with <0.5 µm porosity. Cell confluence on the 4, 40 and 100 µm porosity grade ceramic substrates were irregular with confluent or sub-confluent regions separated by nascent lacunae (FIG. 5C). Though all tissues cultivated on porous substrates remained anchored through day 12, partial tissue release was observed on the ceramic substrate with a <0.5 µm porosity grade, as indicated by the bracket in the figure. Lacunae were visible in tissues cultured on the 4, 40 and 100 µm ceramic substrates (FIG. 5D), as indicated by the arrows in the figure.

In this study, porous substrates were observed to delay tissue release by at least five days, for up to 12 days in culture. Lacunae were not observed within the confluent cultures on the non-porous SS or TCPS substrates, prior to release of their respective tissues. Taken together, these results demonstrate that substrate porosity-maintained tissue anchorage, and given threshold porosity diameter, supported the autologous assembly of lacunae. Our findings that tissues grown on the ceramic substrate with a <0.5 µm porosity grade began release from its substrate prior to tissues grown on the substrates with 4, 40, and 100 µm porosity grades further supports a correlation between tissue anchorage and substrate porosity diameter threshold.

Example 2. Orthogonal Flow and Differential Pressure

Pressure differential across a porous substrate for cell cultivation is a determinant of the pressure cells cultivated on either surface of the substrate are subjected to. To evaluate the pressure differential created across porous materials modeled as substrates for tissue cultivation as a function of orthogonal flow, different substrates with porosity grades ranging from 0.2 to 5 µm were mounted in an orthogonal flow chamber such that fluidic bypass around the substrate was bounded, and therefore directed unidirectionally through the substrate. A peristaltic pump head installed upstream and in-line to the substrate was activated directing orthogonal flow across each substrate at 0.1, 0.3, 0.5, 0.7, 1.0, 3.0, 5.0, 7.0, 10.0, 12.0 and 13.4 ml/min. The inline pressures were recorded by in-line pressure sensors mounted upstream, between the pump head and the fluidics chamber, and downstream, after the fluidics chamber. Line pressure was not independently regulated downstream of the fluidics chamber. To determine the influence of forward and reverse flow on the pressure differential at the substrate, the peristaltic pump head was operated respectively in a clockwise direction (i.e. directing flow towards the porous substrate) and a counterclockwise direction (i.e. directing flow away from the porous substrate) at the targeted flow rates. Upstream and downstream in-line pressure measurement values were recorded for each substrate and at each flow rate. Pressure differentials for each substrate and flow rate were calculated and recorded as the difference between the upstream and downstream line pressure values.

Figure 6A:
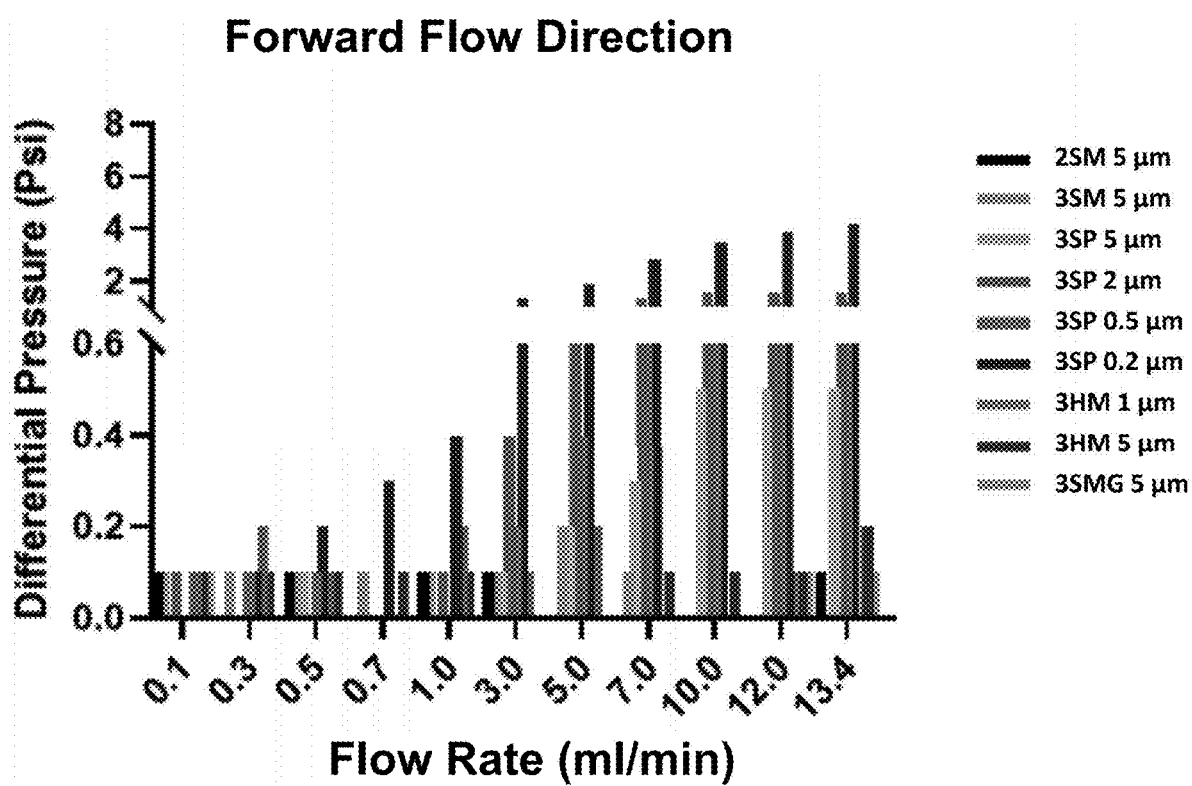
FIG. 6A depicts differential pressure (Y-axis) at porous substrates as a function of flow rate (X-axis) where the fluid is being pumped toward the substrates. Labels in the legend in FIG. 6A represent different substrate porosity grades.
Figure 6B:
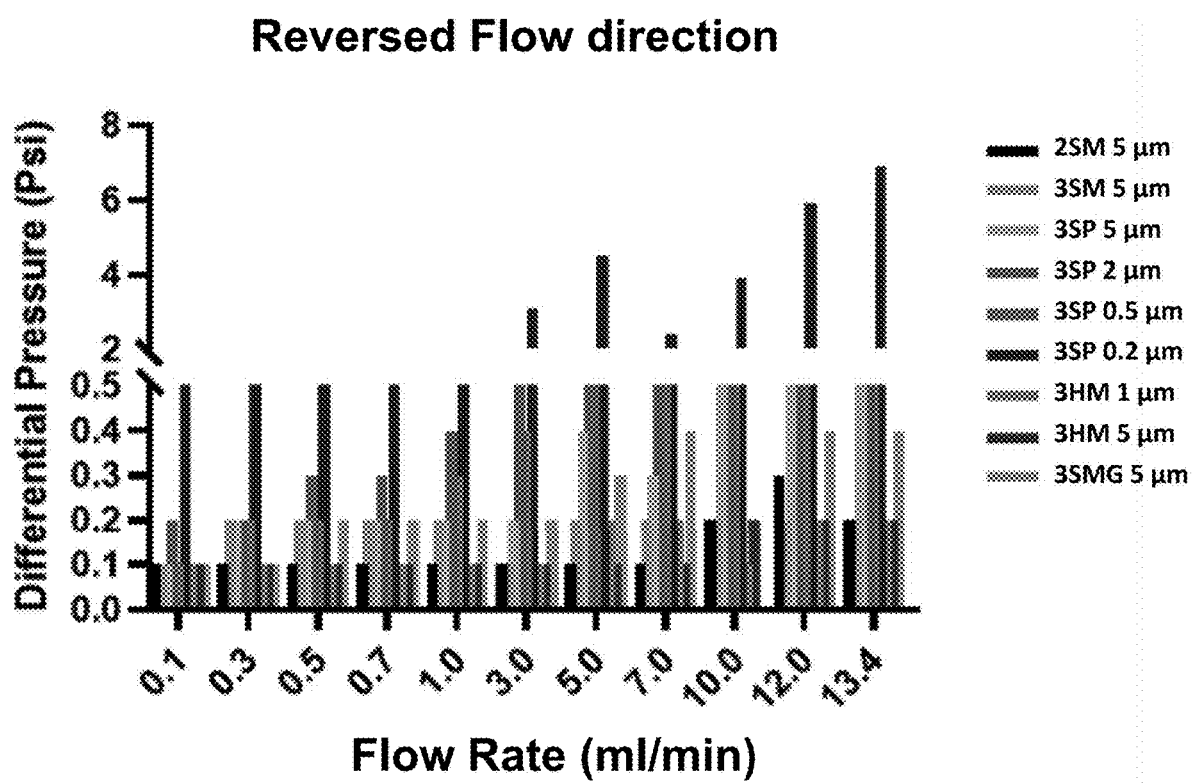
FIG. 6B depicts differential pressure (Y-axis) at porous substrates as a function of flow rate (X-axis) where the fluid is being pumped away from the substrates. Labels in the legend in FIG. 6B represent different substrate porosity grades.

Pressure differentials varied across the substrate as a function of the substrate class, porosity grade, flow direction, and flow rate. Overall, pressure differentials increased with pump speed and flow rate, and decreased porosity size grading, in both the forward and reverse flow directions. However, this observed trend was not always linear. For example, the 3SP class 2 µm grade substrate maintained a higher-pressure differential at higher flow 3SP class 0.5 µm grade in both the forward and the reverse direction. Moreover, the 3SP class 0.2 µm grade and 3SP class 5 µm grade substrates both maintained reduced differential pressures at 7.0 µmL/min under reverse flow relative to their respective differential pressures maintained at 5.0 mL/min under reverse flow. Many of the substrates, including the 2SM, 3SM, 3HM and 3SMG class substrates maintained little to no pressure differential across the flow rate ranges tested, suggesting that higher flow rates are required to create pressure differentials where these substrates are applied. Relative to initial pressure, upstream line pressure changes under forward flow through substrates were positive (FIG. 6A). Under reverse flow, this effect was likewise reversed, and negative pressures changes were observed (FIG. 6B). Taken together, these results demonstrate how precise pressure differentials may be targeted across porous substrates for cultivation of tissues under orthogonal flow.

The foregoing description, for purposes of explanation, used specific nomenclature to provide a thorough understanding of the invention. However, it will be apparent to one skilled in the art that specific details are not required in order to practice the invention. Thus, the foregoing descriptions of specific variations of the invention are presented for purposes of illustration and description. They are not intended to be exhaustive or to limit the invention to the precise forms disclosed; obviously, many modifications and variations are possible in view of the above teachings. The variations were chosen and described in order to explain the principles of the invention and its practical applications. These thereby enable others skilled in the art to utilize the invention and various variations with various modifications as are suited to the particular use contemplated. It is intended that the following claims and their equivalents define the scope of the invention.

The invention claimed is:

1. A method for cultivating a comestible meat product, the method comprising:
    seeding a plurality of a first type of cells onto a side of a porous substrate in a bioreactor;
    seeding a plurality of second type of cells onto an opposing side of the porous substrate in the bioreactor; and
    culturing the plurality of the first type of cells and the plurality of the second type of cells by flowing culture media through the bioreactor, wherein flowing the culture media through the bioreactor causes the plurality of the second type of cells to secrete products that aid in cultivation of the plurality of the first type of cells.

2. The method of claim 1, wherein:
    the plurality of the first type of cells comprises harvest cells; and
    the plurality of the second type of cells comprises feeder cells.

3. The method of claim 2, wherein the feeder cells are not suitable for incorporation into the comestible meat product.

4. The method of claim 2, wherein:
    the first type of cells comprises a non-fibrogenic cell population; and
    the second type of cells comprises a fibrogenic cell population.

5. The method of claim 4, wherein:
    the first type of cells comprises myoblasts; and
    the second type of cells comprises fibroblasts.

6. The method of claim 1, wherein flowing the culture media through the bioreactor causes the plurality of the second type of cells to secrete products that aid in cultivation of the plurality of the first type of cells by supporting one or more of anchorage to the porous substrate, cell growth, or tissue formation.

7. The method of claim 2, wherein the secreted products from the plurality of the second type of cells aid in cultivation of the plurality of the first type of cells without altering a cellular composition of the plurality of the first type of cells.

8. The method of claim 1, wherein flowing the culture media through the bioreactor causes the plurality of the second type of cells to secrete one or more of peptide hormones or extracellular matrix proteins that aid in cultivation of the plurality of the first type of cells.

9. The method of claim 1, wherein flowing the culture media through the bioreactor causes the plurality of the second type of cells to secrete collagen peptides that aid in cultivation of the plurality of the first type of cells.

10. The method of claim 1, wherein flowing the culture media through the bioreactor causes the secrete products to travel through the porous substrate from the plurality of cells of the second type to the plurality of cells of the first type.

11. A method for cultivating a comestible meat product, the method comprising:
    seeding a plurality of cells on a substrate arranged in a bioreactor; and
    cultivating the plurality of cells on the substrate arranged in the bioreactor by flowing culture media through the bioreactor:
        in a forward direction for a first flow interval; and
        in a reverse direction for a second flow interval.

12. The method of claim 11, wherein the substrate is a porous substrate, and flowing the culture media through the bioreactor causes the culture media to enter the porous substrate.

13. The method of claim 12, further comprising alternating a flow of the culture media between the forward direction and the reverse direction to enable attachment and cultivation of cells simultaneously on opposing surfaces of the substrate while reducing porous occlusion.

14. The method of claim 11, wherein flowing the culture media through the bioreactor comprises flowing the culture media at an angle non-parallel to opposing major surfaces of the substrate.

15. The method of claim 14, wherein flowing the culture media through the bioreactor comprises flowing the culture media at an angle of between about 60 degrees and 120 degrees relative to the opposing major surfaces of the substrate.

16. The method of claim 11, wherein:
the first flow interval and the second flow interval form a primary sequence of flow intervals; and
cultivating the plurality of cells on the substrate arranged in the bioreactor by flowing culture media through the bioreactor further comprises flowing the culture media in a secondary sequence of flow intervals.

17. The method of claim 16, wherein the secondary sequence of flow intervals have a duration less than a duration of the primary sequence of flow intervals.

18. The method of claim 16, wherein the primary sequence of flow intervals further includes a static flow interval.

19. The method of claim 11, wherein flowing the culture media through the bioreactor comprises creating a pressure differential across the substrate.

20. The method of claim 11, wherein seeding the plurality of cells on the substrate arranged in the bioreactor comprises alternating a direction of flow of cells through the bioreactor.

\* \* \* \* \*